US010485549B2

(12) United States Patent
Williams et al.

(10) Patent No.: US 10,485,549 B2
(45) Date of Patent: *Nov. 26, 2019

(54) SURGICAL DEVICE, SURGICAL ADAPTERS FOR USE BETWEEN SURGICAL HANDLE ASSEMBLY AND SURGICAL LOADING UNITS, AND METHODS OF USE

(71) Applicant: Covidien LP, Mansfield, MA (US)

(72) Inventors: Justin Williams, Southbury, CT (US); Christopher Kaswer, Avon, CT (US)

(73) Assignee: Covidien LP, Mansfield, MA (US)

( * ) Notice: Subject to any disclaimer, the term of this patent is extended or adjusted under 35 U.S.C. 154(b) by 356 days.

This patent is subject to a terminal disclaimer.

(21) Appl. No.: 15/459,172

(22) Filed: Mar. 15, 2017

(65) Prior Publication Data

US 2017/0181749 A1    Jun. 29, 2017

Related U.S. Application Data

(63) Continuation of application No. 13/853,180, filed on Jul. 9, 2013, now Pat. No. 9,629,633.

(51) Int. Cl.
*A61B 17/115* (2006.01)
*A61B 17/072* (2006.01)
(Continued)

(52) U.S. Cl.
CPC ........ *A61B 17/1155* (2013.01); *A61B 17/072* (2013.01); *A61B 17/07207* (2013.01);
(Continued)

(58) Field of Classification Search
CPC .............. A61B 17/1155; A61B 17/072; A61B 17/07207; A61B 17/3205;
(Continued)

(56) References Cited

U.S. PATENT DOCUMENTS 3,079,606 A    3/1963    Bobrov et al.
3,490,675 A    1/1970    Green et al.
(Continued)

FOREIGN PATENT DOCUMENTS

EP    0634144 A1    1/1995
EP    2446834 A1    5/2012
(Continued)

OTHER PUBLICATIONS

Extended European Search Report corresponding to EP 14 16 2201.9, completed Nov. 3, 2014; and dated Nov. 13, 2014; (7 pp).
(Continued)

*Primary Examiner* — Nathaniel C Chukwurah
*Assistant Examiner* — Lucas E. A. Palmer

(57) ABSTRACT

A surgical device comprising a handle housing, an adapter, an elongated portion, an end effector, a first drive element, and a second drive element is disclosed. The adapter includes a first drive assembly configured to mechanically engage a portion of a first actuation mechanism of the handle housing. The elongated portion is configured to extend distally from the adapter. The first drive element is disposed in mechanical cooperation with the first drive assembly. The second drive element is disposed in mechanical cooperation with the first drive assembly. Rotation of the first drive assembly in a first direction about the longitudinal axis causes distal translation of the first drive element. Rotation of the first drive assembly in a second direction about the longitudinal axis causes distal translation of the second drive element. The first direction is opposite from the second direction.

19 Claims, 16 Drawing Sheets

FIG. 3

(51) Int. Cl.
*A61B 17/3205* (2006.01)
*A61B 17/00* (2006.01)
*A61B 17/29* (2006.01)

(52) U.S. Cl.
CPC ........ *A61B 17/115* (2013.01); *A61B 17/3205* (2013.01); *A61B 2017/0046* (2013.01); *A61B 2017/00389* (2013.01); *A61B 2017/00398* (2013.01); *A61B 2017/00473* (2013.01); *A61B 2017/00477* (2013.01); *A61B 2017/07257* (2013.01); *A61B 2017/07285* (2013.01); *A61B 2017/2903* (2013.01); *A61B 2017/2925* (2013.01)

(58) Field of Classification Search
CPC ........... A61B 2017/00389; A61B 2017/00398; A61B 2017/0046; A61B 2017/00473; A61B 2017/00477; A61B 2017/07257; A61B 2017/07285; A61B 2017/2903; A61B 2017/2925
See application file for complete search history.

(56) References Cited

U.S. PATENT DOCUMENTS

| | | | | |
|---|---|---|---|---|
| 3,618,842 | A * | 11/1971 | Bryan | A61B 17/0684 227/120 |
| 3,638,652 | A | 2/1972 | Kelley | |
| 4,207,873 | A * | 6/1980 | Kruy | A61B 1/0052 600/146 |
| 4,331,277 | A | 5/1982 | Green | |
| 4,349,028 | A | 9/1982 | Green | |
| 4,473,077 | A | 9/1984 | Noiles et al. | |
| 4,485,817 | A | 12/1984 | Swiggett | |
| 4,488,523 | A | 12/1984 | Shichman | |
| 4,499,895 | A | 2/1985 | Takayama | |
| 4,576,167 | A | 3/1986 | Noiles | |
| 4,589,412 | A | 5/1986 | Kensey | |
| 4,603,693 | A * | 8/1986 | Conta | A61B 17/1155 227/179.1 |
| 4,606,343 | A * | 8/1986 | Conta | A61B 17/115 227/178.1 |
| 4,688,555 | A | 8/1987 | Wardle | |
| 4,941,466 | A | 7/1990 | Romano | |
| 4,991,763 | A | 2/1991 | Storace | |
| 5,005,749 | A | 4/1991 | Aranyi | |
| 5,114,065 | A | 5/1992 | Storace | |
| 5,119,983 | A | 6/1992 | Green et al. | |
| 5,192,292 | A * | 3/1993 | Cezana | A61B 17/32002 604/22 |
| 5,201,750 | A * | 4/1993 | Hocherl | A61B 17/22 600/568 |
| 5,207,691 | A | 5/1993 | Nardella | |
| 5,219,111 | A | 6/1993 | Bilotti et al. | |
| 5,249,583 | A * | 10/1993 | Mallaby | A61B 10/0275 600/567 |
| 5,256,149 | A * | 10/1993 | Banik | A61B 17/3421 604/164.01 |
| 5,258,007 | A | 11/1993 | Spetzler et al. | |
| 5,258,008 | A | 11/1993 | Wilk | |
| 5,271,543 | A | 12/1993 | Grant et al. | |
| 5,271,544 | A | 12/1993 | Fox et al. | |
| 5,275,322 | A | 1/1994 | Brinkerhoff et al. | |
| 5,285,945 | A | 2/1994 | Brinkerhoff et al. | |
| 5,292,053 | A | 3/1994 | Bilotti et al. | |
| 5,292,326 | A | 3/1994 | Green et al. | |
| 5,336,229 | A | 8/1994 | Noda | |
| 5,348,259 | A | 9/1994 | Blanco et al. | |
| 5,383,880 | A | 1/1995 | Hooven | |
| 5,433,721 | A | 7/1995 | Hooven et al. | |
| 5,452,836 | A | 9/1995 | Huitema et al. | |
| 5,465,894 | A | 11/1995 | Clark et al. | |
| 5,467,911 | A | 11/1995 | Tsuruta et al. | |
| 5,482,197 | A | 1/1996 | Green et al. | |
| 5,509,918 | A | 4/1996 | Romano | |
| 5,549,637 | A | 8/1996 | Crainich | |
| 5,553,675 | A | 9/1996 | Pitzen et al. | |
| 5,564,615 | A | 10/1996 | Bishop et al. | |
| 5,571,116 | A * | 11/1996 | Bolanos | A61B 17/07207 227/175.3 |
| 5,580,067 | A | 12/1996 | Hamblin et al. | |
| 5,588,580 | A | 12/1996 | Paul et al. | |
| 5,588,581 | A | 12/1996 | Conlon et al. | |
| 5,601,224 | A | 2/1997 | Bishop et al. | |
| 5,609,560 | A | 3/1997 | Ichikawa et al. | |
| 5,626,587 | A | 5/1997 | Bishop et al. | |
| 5,634,584 | A | 6/1997 | Okorocha et al. | |
| 5,662,662 | A | 9/1997 | Bishop et al. | |
| 5,676,674 | A | 10/1997 | Bolanos et al. | |
| 5,680,981 | A | 10/1997 | Mililli et al. | |
| 5,685,474 | A * | 11/1997 | Seeber | A61B 17/115 227/175.1 |
| 5,732,871 | A | 3/1998 | Clark et al. | |
| 5,779,130 | A | 7/1998 | Alesi et al. | |
| 5,792,165 | A * | 8/1998 | Klieman | A61B 17/29 606/170 |
| 5,842,993 | A * | 12/1998 | Eichelberger | A61B 1/0051 600/462 |
| 5,865,361 | A | 2/1999 | Milliman et al. | |
| 5,868,760 | A | 2/1999 | McGuckin, Jr. | |
| 5,915,616 | A | 6/1999 | Viola et al. | |
| 5,954,259 | A * | 9/1999 | Viola | A61B 17/07207 227/176.1 |
| 5,964,394 | A | 10/1999 | Robertson | |
| 5,993,454 | A * | 11/1999 | Longo | A61B 17/1624 606/80 |
| 6,050,989 | A * | 4/2000 | Fox | A61B 17/32002 285/184 |
| 6,119,913 | A | 9/2000 | Adams et al. | |
| 6,126,058 | A | 10/2000 | Adams et al. | |
| 6,165,169 | A | 12/2000 | Panescu et al. | |
| 6,193,129 | B1 | 2/2001 | Bittner et al. | |
| 6,202,914 | B1 | 3/2001 | Geiste et al. | |
| 6,241,139 | B1 | 6/2001 | Milliman et al. | |
| 6,264,087 | B1 | 7/2001 | Whitman | |
| 6,269,997 | B1 * | 8/2001 | Balazs | A61B 17/115 227/175.1 |
| 6,505,768 | B2 | 1/2003 | Whitman | |
| 6,517,565 | B1 * | 2/2003 | Whitman | A61B 17/07207 600/146 |
| 6,520,971 | B1 | 2/2003 | Perry et al. | |
| 6,530,932 | B1 | 3/2003 | Swayze et al. | |
| 6,698,643 | B2 | 3/2004 | Whitman | |
| 6,743,240 | B2 | 6/2004 | Smith et al. | |
| 6,824,548 | B2 | 11/2004 | Smith et al. | |
| 6,835,199 | B2 | 12/2004 | McGuckin, Jr. et al. | |
| 6,843,403 | B2 | 1/2005 | Whitman | |
| 7,114,642 | B2 | 10/2006 | Whitman | |
| 7,549,563 | B2 | 6/2009 | Mather et al. | |
| 7,556,185 | B2 | 7/2009 | Viola | |
| 7,575,144 | B2 | 8/2009 | Ortiz et al. | |
| 7,588,175 | B2 | 9/2009 | Timm et al. | |
| 7,708,182 | B2 | 5/2010 | Viola | |
| 7,721,930 | B2 * | 5/2010 | McKenna | A61B 17/00491 227/175.1 |
| 7,721,931 | B2 | 5/2010 | Shelton, IV et al. | |
| 7,738,971 | B2 | 6/2010 | Swayze et al. | |
| 7,766,207 | B2 | 8/2010 | Mather et al. | |
| 7,770,776 | B2 | 8/2010 | Chen et al. | |
| 7,793,812 | B2 | 9/2010 | Moore et al. | |
| 7,803,151 | B2 | 9/2010 | Whitman | |
| 7,909,221 | B2 | 3/2011 | Viola et al. | |
| 7,918,230 | B2 * | 4/2011 | Whitman | A61B 17/07207 128/898 |
| 7,922,061 | B2 | 4/2011 | Shelton, IV et al. | |
| 7,922,063 | B2 * | 4/2011 | Zemlok | A61B 17/07207 227/176.1 |
| 7,975,895 | B2 | 7/2011 | Milliman | |
| 8,025,199 | B2 | 9/2011 | Whitman et al. | |
| 8,035,487 | B2 | 10/2011 | Malackowski | |
| 8,038,044 | B2 | 10/2011 | Viola | |
| 8,181,840 | B2 | 5/2012 | Milliman | |

(56) References Cited

U.S. PATENT DOCUMENTS

| | | | |
|---|---|---|---|
| 8,202,290 B2* | 6/2012 | Smith | A61B 17/32093 606/185 |
| 8,317,075 B2 | 11/2012 | Milliman | |
| 8,348,855 B2 | 1/2013 | Hillely et al. | |
| 8,708,211 B2* | 4/2014 | Zemlok | A61B 17/07207 227/175.1 |
| 8,758,391 B2 | 6/2014 | Swayze et al. | |
| 8,806,973 B2 | 8/2014 | Ross et al. | |
| 8,875,972 B2 | 11/2014 | Weisenburgh, II et al. | |
| 8,893,946 B2 | 11/2014 | Boudreaux et al. | |
| 8,899,462 B2 | 12/2014 | Kostrzewski et al. | |
| 8,939,344 B2 | 1/2015 | Olson et al. | |
| 8,960,519 B2 | 2/2015 | Whitman et al. | |
| 8,961,396 B2 | 2/2015 | Azarbarzin et al. | |
| 8,968,276 B2 | 3/2015 | Zemlok et al. | |
| 8,968,312 B2* | 3/2015 | Marczyk | A61B 17/29 606/51 |
| 8,968,337 B2 | 3/2015 | Whitfield et al. | |
| 8,992,422 B2 | 3/2015 | Spivey et al. | |
| 9,064,653 B2 | 6/2015 | Prest et al. | |
| 9,072,536 B2* | 7/2015 | Shelton, IV | A61B 34/30 |
| 9,113,875 B2 | 8/2015 | Viola et al. | |
| 9,216,013 B2 | 12/2015 | Scirica et al. | |
| 9,282,961 B2 | 3/2016 | Whitman et al. | |
| 9,282,963 B2 | 3/2016 | Bryant | |
| 9,295,522 B2 | 3/2016 | Kostrzewski | |
| 9,307,986 B2 | 4/2016 | Hall et al. | |
| 9,629,633 B2 | 4/2017 | Williams et al. | |
| 2002/0049454 A1 | 4/2002 | Whitman et al. | |
| 2002/0165541 A1 | 11/2002 | Whitman | |
| 2003/0130677 A1* | 7/2003 | Whitman | A61B 17/072 606/167 |
| 2003/0132268 A1* | 7/2003 | Whitman | A61B 17/07207 227/180.1 |
| 2003/0165794 A1 | 9/2003 | Matoba | |
| 2005/0049616 A1* | 3/2005 | Rivera | A61B 17/1285 606/143 |
| 2005/0125010 A1 | 6/2005 | Smith et al. | |
| 2005/0187576 A1* | 8/2005 | Whitman | A61B 17/115 606/219 |
| 2005/0205640 A1 | 9/2005 | Milliman | |
| 2006/0142740 A1 | 6/2006 | Sherman et al. | |
| 2007/0023476 A1 | 2/2007 | Whitman et al. | |
| 2007/0023477 A1* | 2/2007 | Whitman | A61B 17/07207 227/175.1 |
| 2007/0088343 A1 | 4/2007 | McIntyre et al. | |
| 2007/0270790 A1* | 11/2007 | Smith | A61B 17/1114 606/32 |
| 2008/0077159 A1* | 3/2008 | Madhani | A61B 17/00234 606/130 |
| 2008/0167736 A1 | 7/2008 | Swayze et al. | |
| 2008/0223903 A1* | 9/2008 | Marczyk | A61B 17/072 227/175.1 |
| 2008/0237296 A1 | 10/2008 | Boudreaux et al. | |
| 2008/0251568 A1* | 10/2008 | Zemlok | A61B 17/068 227/175.1 |
| 2008/0257935 A1* | 10/2008 | Viola | A61B 17/07207 227/176.1 |
| 2008/0308603 A1 | 12/2008 | Shelton et al. | |
| 2009/0090763 A1 | 4/2009 | Zemlok et al. | |
| 2009/0090764 A1 | 4/2009 | Viola | A61B 17/07207 227/176.1 |
| 2009/0171242 A1* | 7/2009 | Hibner | A61B 10/0275 600/566 |
| 2009/0236399 A1 | 9/2009 | Bilotti | |
| 2009/0312773 A1* | 12/2009 | Cabrera | A61B 17/0469 606/144 |
| 2010/0089974 A1* | 4/2010 | Shelton, IV | A61B 17/07207 227/180.1 |
| 2010/0193568 A1 | 8/2010 | Scheib et al. | |
| 2010/0211053 A1 | 8/2010 | Ross et al. | |
| 2011/0036892 A1* | 2/2011 | Marczyk | A61B 17/07207 227/176.1 |
| 2011/0046624 A1* | 2/2011 | Lin | A61B 17/00008 606/51 |
| 2011/0071508 A1 | 3/2011 | Duval et al. | |
| 2011/0139852 A1 | 6/2011 | Zingman | |
| 2011/0155786 A1 | 6/2011 | Shelton, IV | |
| 2011/0172648 A1 | 7/2011 | Jeong | |
| 2011/0174099 A1* | 7/2011 | Ross | A61B 17/072 74/89.32 |
| 2011/0208211 A1 | 8/2011 | Whitfield et al. | |
| 2011/0276057 A1 | 11/2011 | Conlon et al. | |
| 2012/0074199 A1 | 3/2012 | Olson et al. | |
| 2012/0089131 A1 | 4/2012 | Zemlok et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0245428 A1 | 9/2012 | Smith et al. | |
| 2012/0330285 A1 | 12/2012 | Hartoumbekis et al. | |
| 2013/0093149 A1 | 4/2013 | Saur et al. | |
| 2013/0181035 A1 | 7/2013 | Milliman | |
| 2013/0184704 A1 | 7/2013 | Beardsley et al. | |
| 2013/0274722 A1 | 10/2013 | Kostrzewski et al. | |
| 2013/0282052 A1* | 10/2013 | Aranyi | A61B 17/07207 606/208 |
| 2013/0324978 A1 | 12/2013 | Nicholas et al. | |
| 2013/0324979 A1 | 12/2013 | Nicholas et al. | |
| 2013/0334281 A1 | 12/2013 | Williams | |
| 2014/0025046 A1* | 1/2014 | Williams | A61B 17/07207 606/1 |
| 2014/0100558 A1* | 4/2014 | Schmitz | A61B 17/3478 606/33 |
| 2014/0107673 A1* | 4/2014 | Snyder | A61B 17/0469 606/148 |
| 2014/0207125 A1 | 7/2014 | Applegate et al. | |
| 2014/0214097 A1* | 7/2014 | Jackson | A61B 17/7037 606/305 |
| 2014/0352463 A1* | 12/2014 | Parihar | F16H 19/02 74/25 |
| 2014/0373652 A1 | 12/2014 | Zergiebel et al. | |
| 2015/0157321 A1 | 6/2015 | Zergiebel et al. | |
| 2015/0164502 A1 | 6/2015 | Richard et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1* | 4/2016 | Cabrera | A61B 17/1155 606/1 |
| 2016/0113648 A1 | 4/2016 | Zergiebel et al. | |
| 2016/0113649 A1 | 4/2016 | Zergiebel et al. | |
| 2016/0270791 A1* | 9/2016 | Williams | A61B 17/068 |
| 2016/0296234 A1* | 10/2016 | Richard | A61B 17/1155 |

FOREIGN PATENT DOCUMENTS

| | | |
|---|---|---|
| EP | 2668910 A2 | 12/2013 |
| FR | 2961682 A1 | 12/2011 |
| JP | 2004513738 A | 5/2004 |
| JP | 2010 540041 A | 12/2010 |
| JP | 2011507653 A | 3/2011 |
| JP | 2011172931 A | 9/2011 |
| JP | 2012096010 A | 5/2012 |
| JP | 2013132559 A | 7/2013 |
| JP | 2015529142 A | 10/2015 |
| KR | 20120022521 A | 3/2012 |
| WO | 0072765 A1 | 12/2000 |
| WO | 0241791 A1 | 5/2002 |

(56) References Cited

FOREIGN PATENT DOCUMENTS

| WO | 20090039510 A1 | 3/2009 |
|----|----------------|--------|
| WO | 2009133875 A1 | 11/2009 |
| WO | 2014/047245 A1 | 3/2014 |

OTHER PUBLICATIONS

European Search Report for EP 08251443.1-2310 date of completion is Mar. 19, 2010 (7 pages).
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 38071 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Extended European Search Report issued in EP 16176996 dated Mar. 2, 2017.
Extended European Search Report issued in corresponding to EP 16176996 dated Mar. 2, 2017.
Japanese Office Action isused in Japanese Application No. 2014-063584 dated May 11, 2018.
Japanese Office Action issued in corresponding Japanese Application No. 2014-063584 dated Nov. 29, 2017.

* cited by examiner

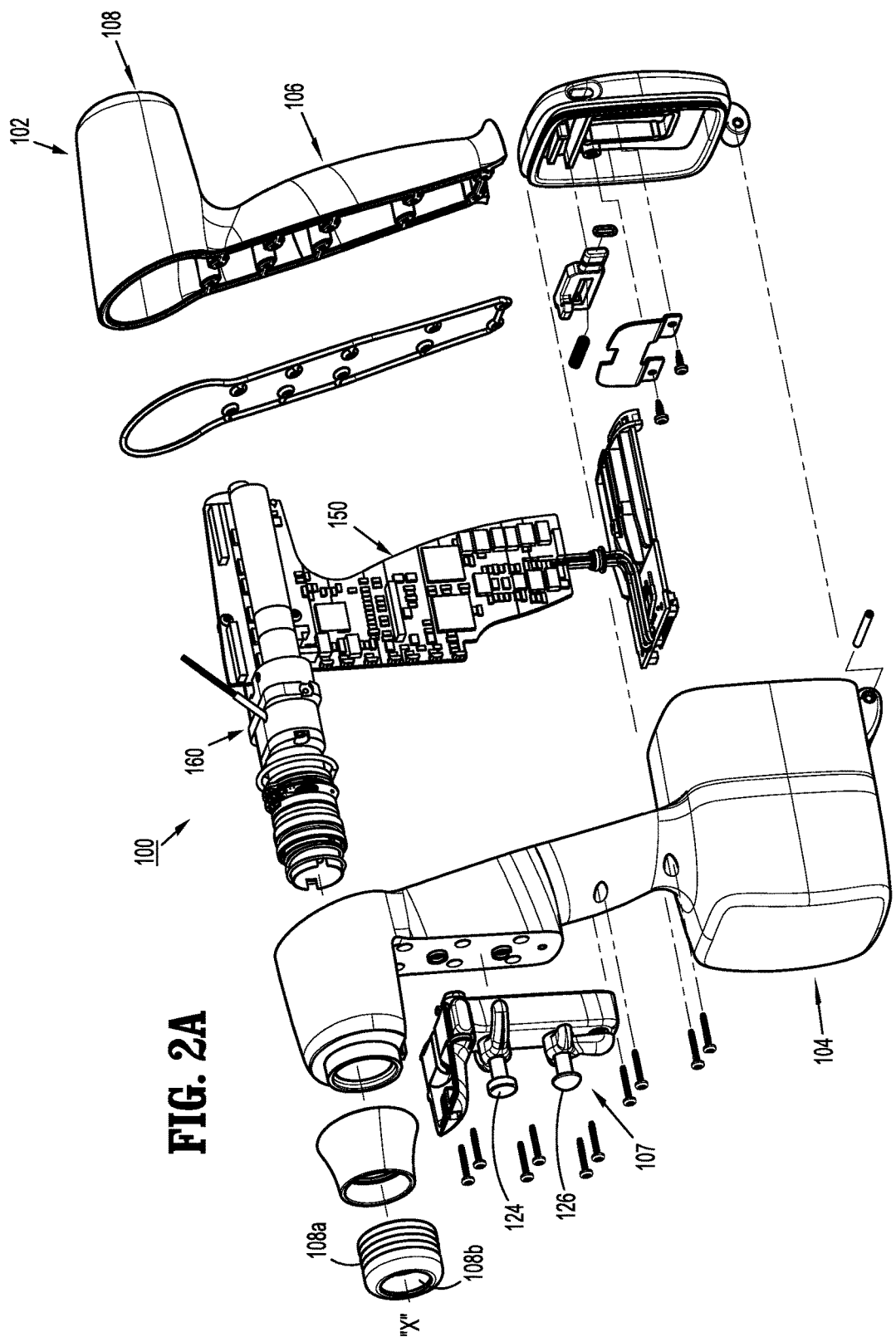

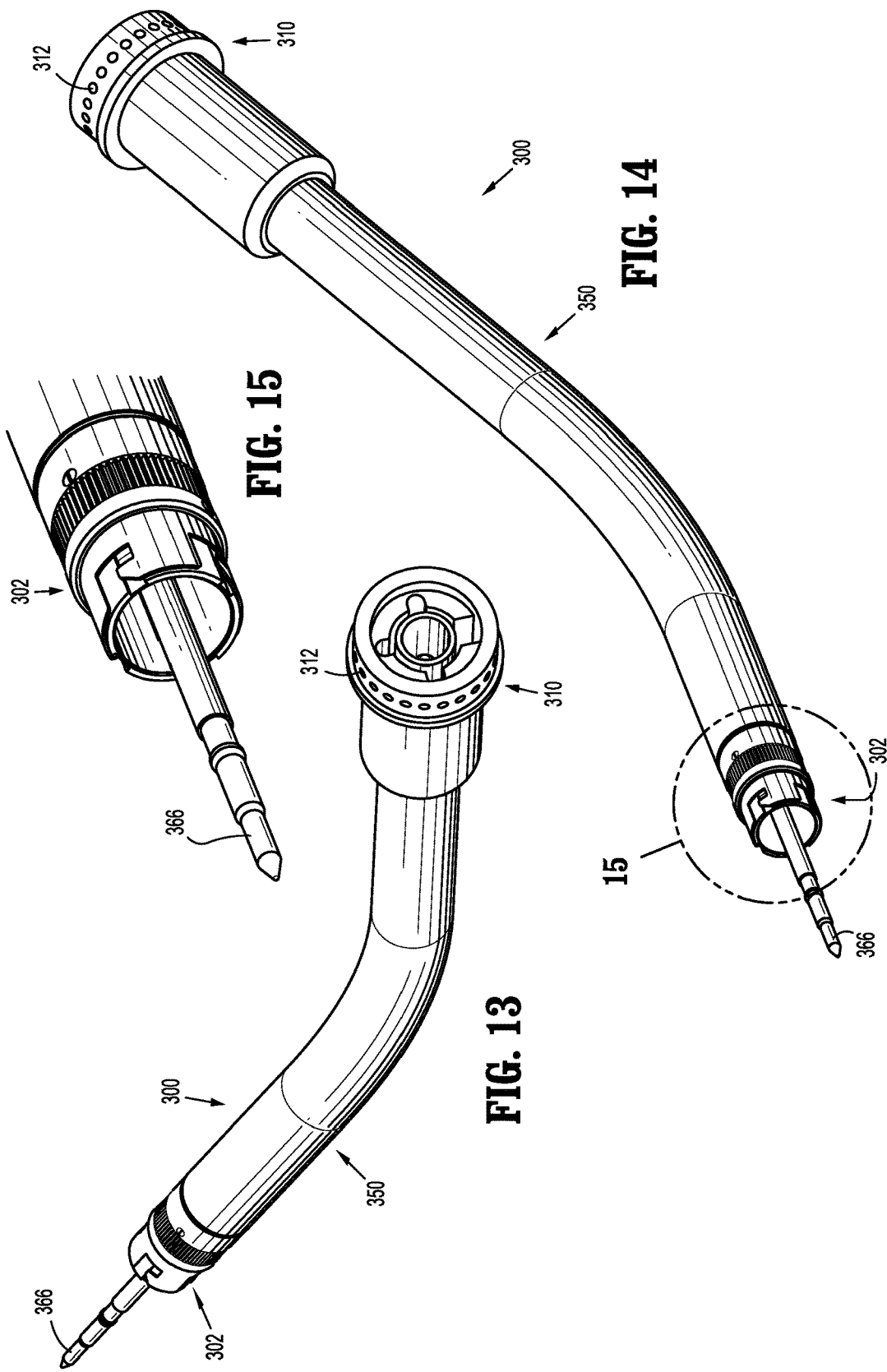

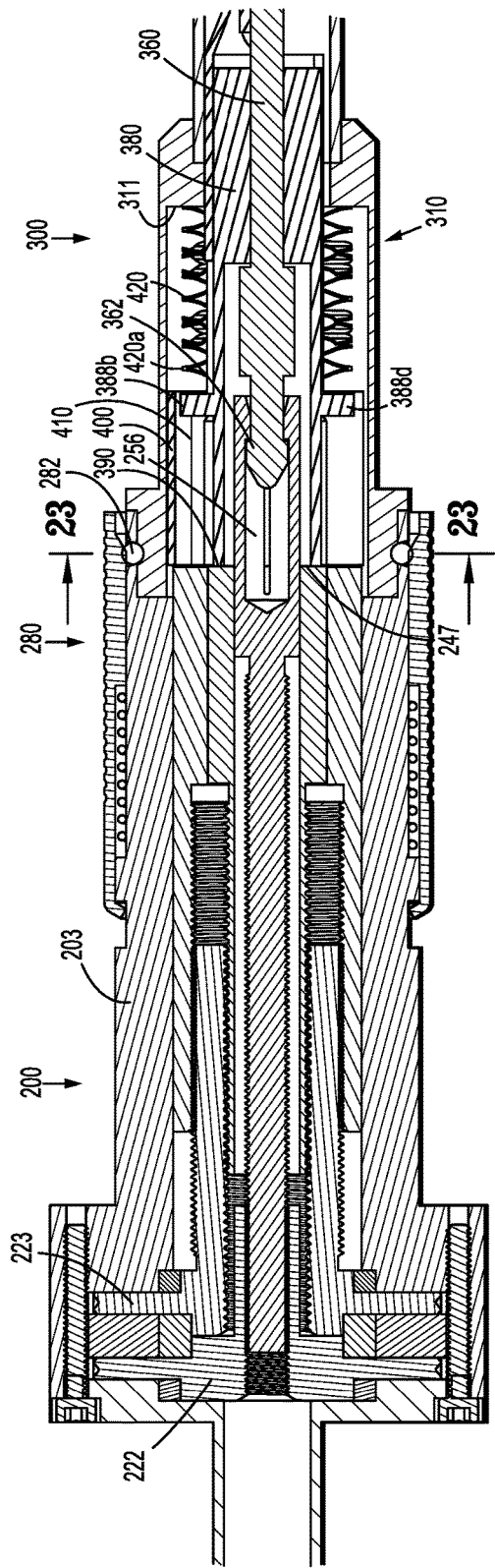

SURGICAL DEVICE, SURGICAL ADAPTERS FOR USE BETWEEN SURGICAL HANDLE ASSEMBLY AND SURGICAL LOADING UNITS, AND METHODS OF USE

CROSS-REFERENCE TO RELATED APPLICATIONS

This application is a continuation of U.S. patent application Ser. No. 13/853,180 filed Jul. 9, 2013, and the disclosure of the above-identified application is hereby incorporated by reference in its entirety.

BACKGROUND

1. Technical Field

The present disclosure relates to surgical devices and/or systems, surgical adapters and their methods of use. More specifically, the present disclosure relates to hand held powered surgical devices, surgical adapters and/or adapter assemblies for use between and for interconnecting the powered, rotating and/or articulating surgical device or handle assembly and a loading unit for clamping, cutting and/or stapling tissue.

2. Background of Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil rod with attached anvil head is mounted to the distal end of the instrument adjacent the staple holding component. Opposed end portions of tissue of the hollow organ(s) to be stapled are clamped between the anvil head and the staple holding component. The clamped tissue is stapled by driving one or more staples from the staple holding component so that the ends of the staples pass through the tissue and are deformed by the anvil head. An annular knife is advanced to core tissue with the hollow organ to free a tubular passage within the organ.

Another type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable loading unit or the like that is selectively connected to the handle assembly prior to use and then disconnected from the loading unit following use in order to be disposed of or in some instances sterilized for re-use.

Many of the existing loading units for use with many of the existing surgical devices and/or handle assemblies are driven by a linear force. For examples, loading units for performing endo-gastrointestinal anastomosis procedures, end-to-end anastomosis procedures and transverse anastomosis procedures, each typically require a linear driving force in order to be operated. As such, these loading units are not compatible with surgical devices and/or handle assemblies that use a rotary motion to deliver power or the like.

In order to make the linear driven loading units compatible with surgical devices and/or handle assemblies that use a rotary motion to deliver power, a need exists for adapters and/or adapter assemblies to interface between and interconnect the linear driven loading units with the rotary driven surgical devices and/or handle assemblies.

SUMMARY

The present disclosure relates to a surgical device comprising a handle housing, an adapter, an elongated portion, an end effector, a first drive element, and a second drive element. The handle housing supports a first actuation mechanism. The adapter is configured to mechanically engage the first actuation mechanism. The elongated portion is configured to extend distally from the adapter and defines a longitudinal axis. The end effector is configured to mechanically engage a distal portion of the elongated portion. The first drive element is disposed in mechanical cooperation with the first drive assembly. The second drive element is disposed in mechanical cooperation with the first drive assembly. Rotation of the first drive assembly in a first direction about the longitudinal axis causes distal translation of the first drive element. Rotation of the first drive assembly in a second direction about the longitudinal axis causes distal translation of the second drive element. The first direction is opposite from the second direction.

In disclosed embodiments, rotation of the first drive assembly in the first direction causes proximal translation of at least a portion of the second drive element. Here, it is disclosed that rotation of the first drive assembly in the second direction causes proximal translation of at least a portion of the first drive element. It is further disclosed that the end effector includes a plurality of fasteners therein, and that distal translation of the first drive element causes the fasteners to be ejected from the end effector. It is further disclosed that the end effector includes a knife therein, and that distal translation of the second drive element causes the knife to be distally translated.

In disclosed embodiments, the surgical device further comprises a second actuation mechanism support by the handle housing, a second drive assembly disposed at least partially within the adapter and in mechanical cooperation with a portion of the second actuation mechanism, and a third drive element disposed in mechanical cooperation with the second drive assembly. Here, actuation of the second actuation mechanism causes proximal translation of at least a portion of the third drive element. If is further disclosed that proximal translation of the third drive element causes an anvil assembly of the end effector to move toward a cartridge assembly of the end effector.

In disclosed embodiments, the first drive assembly includes a set of right-handed threads and a set of left-handed threads. Here, it is disclosed that the first drive element is configured to mechanically engage the set of right-handed threads, and the second drive element is configured to mechanically engage the set of left-handed threads. It is further disclosed that the right-handed threads are disposed about an outside diameter of a portion of the first drive assembly, and the left-handed threads are disposed about in inside diameter of a portion of the first drive assembly.

In disclosed embodiment, the first drive element includes a proximal portion disposed at least partially within the adapter and a distal portion disposed at least partially within the elongated portion, and the second drive element includes a proximal portion disposed at least partially within the adapter and a distal portion disposed at least partially within the elongated portion. Here, it is disclosed that each of the proximal portion of the first drive element and the proximal portion of the second drive element are rotationally fixed with respect to each other and with respect to an adapter housing. It is further disclosed that the surgical device comprising a biasing element configured to simultaneously proximally bias the distal portions of the first and second drive elements.

The present disclosure also relates to a surgical device comprising a handle housing, a drive assembly, an elongated portion, a first drive element, and a second drive element. The handle housing supports an actuation mechanism. The drive assembly is disposed in mechanical cooperation with a portion of the actuation mechanism. The elongated portion extends distally from the adapter and defines a longitudinal axis. The end effector is disposed adjacent a distal portion of the elongated portion. The first drive element is threadably engaged with the drive assembly. The second drive element is threadably engaged with the drive assembly. Rotation of the drive assembly in a first direction about the longitudinal axis results in distal translation of the first drive element to effect a first surgical function. Rotation of the drive assembly in a second direction about the longitudinal axis results in distal translation of the second drive element to effect a second function. The first direction is opposite from the second direction, and the first surgical function is different from the second surgical function.

In disclosed embodiments, the first surgical function includes ejecting fasteners from a cartridge assembly toward tissue, and the second surgical function includes distally advancing a knife to sever tissue.

In disclosed embodiments, the drive assembly includes a set of right-handed threads and a set of left-handed threads. Here, it is disclosed that the first drive element is configured to mechanically engage the set of right-handed threads, and the second drive element is configured to mechanically engage the set of left-handed threads. It is further disclosed that the right-handed threads are disposed about an outside diameter of a portion of the drive assembly, and the left-handed threads are disposed about in inside diameter of a portion of the drive assembly.

The present disclosure also relates to a surgical adapter for mechanically engaging a powered assembly having an actuation mechanism. The surgical adapter comprises a drive assembly disposed in mechanical cooperation with a portion of the actuation mechanism, a first drive element threadably engaged with the drive assembly, and a second drive element threadably engaged with the drive assembly. Rotation of the drive assembly in a first direction results in distal translation of the first drive element to effect a first surgical function, and rotation of the drive assembly in a second direction results in distal translation of the second drive element to effect a second function. The first direction is opposite from the second direction, and the first surgical function is different from the second surgical function.

In disclosed embodiments, the drive assembly includes a set of right-handed threads and a set of left-handed threads. The first drive element is configured to mechanically engage the set of right-handed threads, and the second drive element is configured to mechanically engage the set of left-handed threads.

BRIEF DESCRIPTION OF THE DRAWINGS

Embodiments of the present disclosure are described herein with reference to the accompanying drawings, wherein:

FIG. 2A is a perspective view, with parts separated, of a portion of the surgical device of FIGS. 1 and 2;

FIGS. 13 and 14 are perspective views of a tube assembly of the surgical instrument of the present disclosure;

FIG. 15 depicts the portion of the tube assembly indicated in FIG. 14;

FIG. 20 is an enlarged view of the area of detail depicted in FIG. 18;

FIG. 21 is an enlarged view of the area of detail depicted in FIG. 19;

DETAILED DESCRIPTION OF EMBODIMENTS

Figure 1:
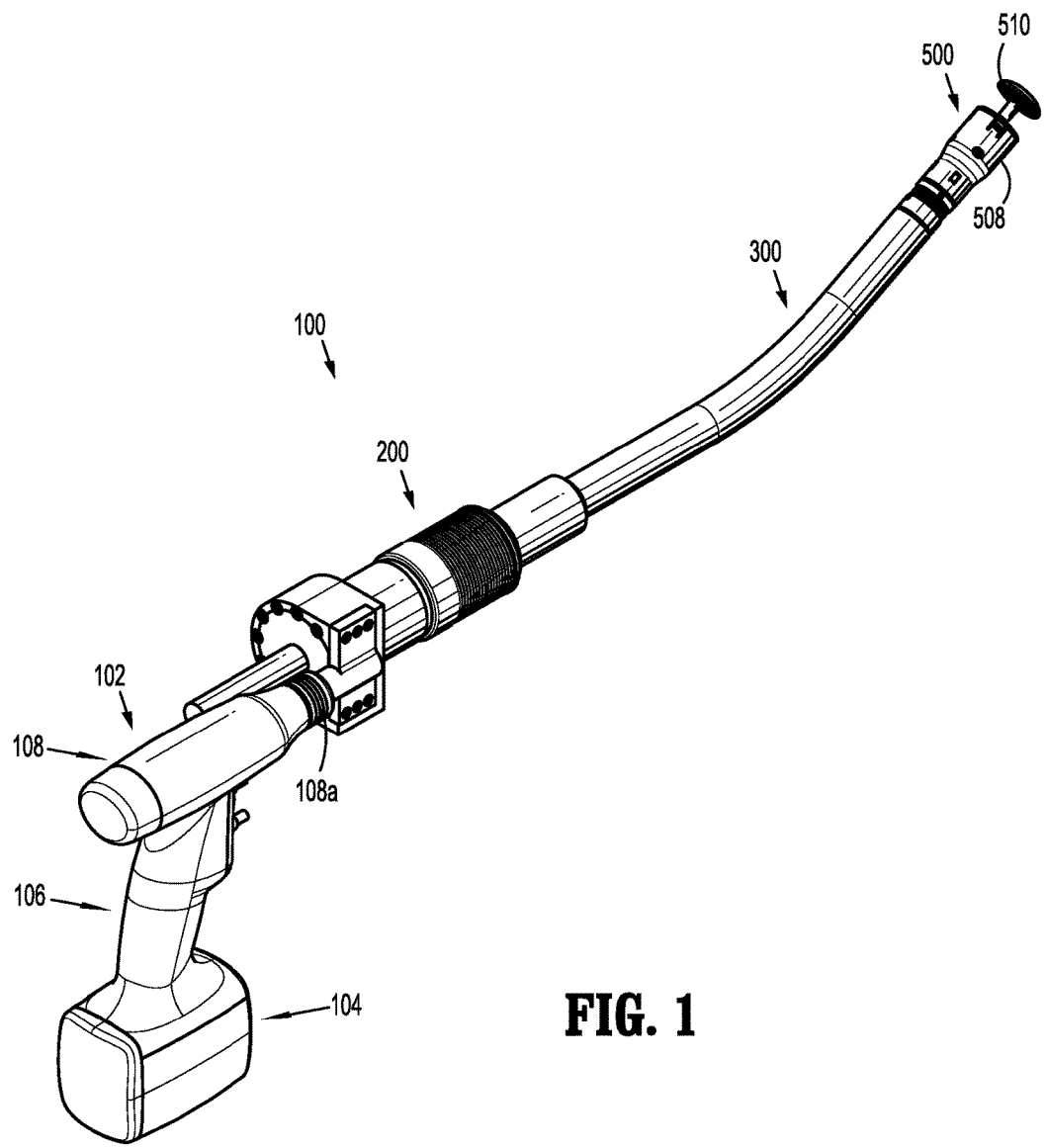
FIG. 1 is a perspective view of a surgical device, including a surgical adapter, in accordance with an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is shown in the form of a powered hand held electromechanical instrument configured for selective attachment thereto of a plurality of different loading units that are each configured for actuation and manipulation by the powered hand held electromechanical surgical instrument.

As illustrated in FIG. 1, surgical device 100 is configured for selective connection with an adapter 200, and, in turn, adapter 200 is configured for selective connection with a loading unit 300 (e.g., a reusable loading unit or a single use loading unit).

Figure 2:
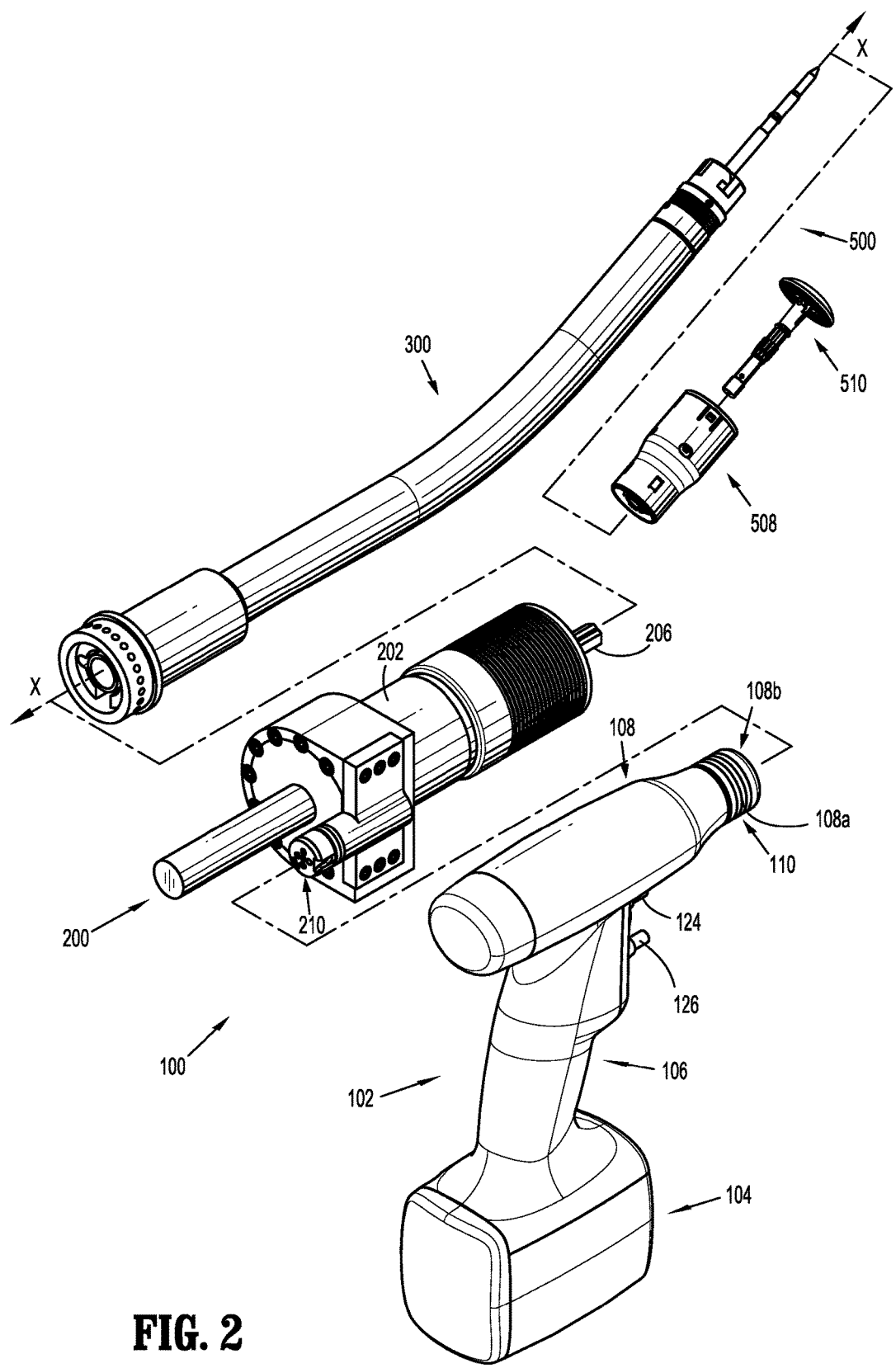
FIG. 2 is a perspective view, with parts separated, of the surgical device and adapter of FIG. 1.

As illustrated in FIGS. 1-2A, surgical device 100 includes a handle assembly or handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 of handle housing 102 provides a housing in which a circuit board 150 (FIG. 2A) is situated. Circuit board 150 is configured to control various operations of surgical device 100, as will be set forth in additional detail below.

Lower housing portion 104 of surgical device 100 defines an aperture formed in an upper surface thereof and which is located beneath or within intermediate housing portion 106. The aperture of lower housing portion 104 provides a passage through which wires pass to electrically interconnect electrical components (e.g., a battery) situated in lower housing portion 104 with electrical components (e.g., circuit board 150 and a drive mechanism 160) situated in intermediate housing portion 106 and/or upper housing portion 108. A trigger housing 107 on a distal surface or side of intermediate housing portion 108 supports a pair of finger-actuated control buttons 124, 126 or actuation mechanisms, which communicate with circuit board 150 to control the drive connectors of surgical device 100. As can be appreciated, handle assembly 102 can include any suitable type and number of actuation mechanisms for actuating the drive connectors.

With specific reference to FIG. 2A, upper housing portion 108 of handle housing 102 provides a housing in which drive mechanism 160 is situated. Drive mechanism 160 is configured to drive shafts and/or gear components in order to perform the various operations of surgical device 100. In particular, drive mechanism 160 is configured to drive shafts and/or gear components in order to selectively move anvil assembly 510 relative to cartridge assembly 508 of loading unit 300, to eject fasteners from cartridge assembly 510, and/or to longitudinally advance a knife. Further details of the electrical components (e.g., circuit board, battery and drive mechanism) are disclosed in U.S. Provisional Patent Application Ser. No. 61/659,116, filed on Jun. 13, 2012, entitled "Apparatus for Endoscopic Procedures," the entire content of which being incorporated herein by reference.

As illustrated in FIGS. 1-2A, a distal section 110 of upper housing portion 108 defines a connecting portion 108a configured to accept a corresponding drive coupling assembly 210 of adapter 200. As illustrated in FIG. 2, connecting portion 108a of surgical device 100 has a cylindrical recess 108b that receives drive coupling assembly 210 of adapter 200 when adapter 200 is mated to surgical device 100. Connecting portion 108a houses two rotatable drive connectors, which are disposed in mechanical cooperation with drive mechanism 160.

Figure 3:
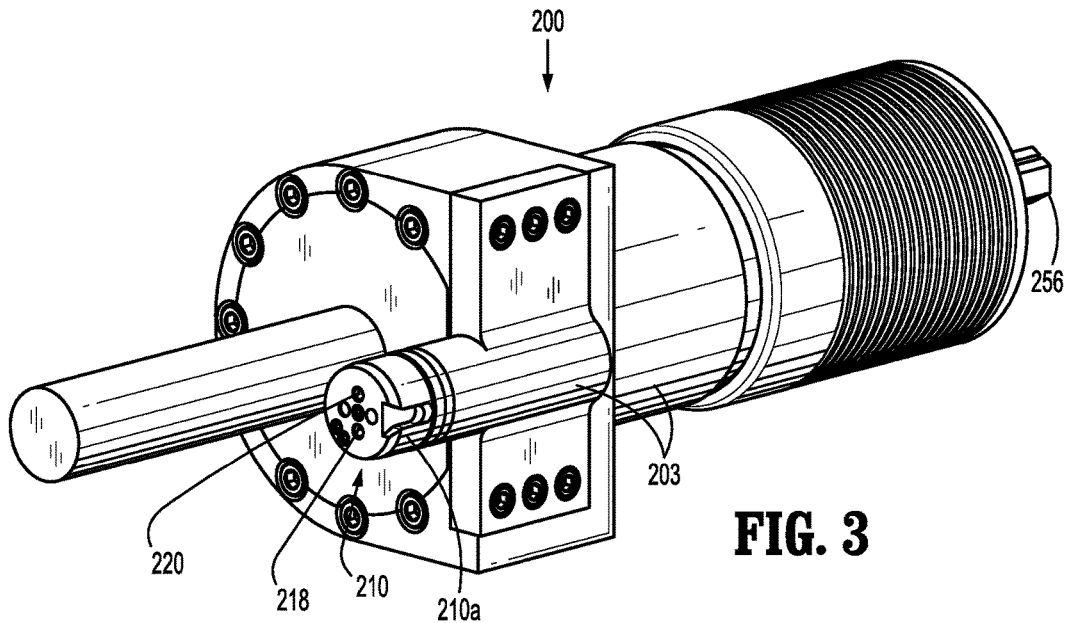
FIGS. 3 and 4 are perspective views of the surgical adapter of FIGS. 1 and 2.

When adapter 200 is mated to surgical device 100, each rotatable drive connector of surgical device 100 couples with a corresponding rotatable connector sleeve 218, 220 of adapter 200 (see FIG. 3). In this regard, the interface between the first drive connector and first connector sleeve 218, and the interface between the second drive connector and second connector sleeve 220 are keyed such that rotation of each drive connector of surgical device 100 causes a corresponding rotation of the corresponding connector sleeve 218, 220 of adapter 200.

The mating of the drive connectors of surgical device 100 with connector sleeves 218, 220 of adapter 200 allows rotational forces to be independently transmitted via each of the respective connector interfaces. The drive connectors of surgical device 100 are configured to be independently rotated by drive mechanism 160. In this regard, a function selection module of drive mechanism 160 selects which drive connector or connectors of surgical device 100 is to be driven by an input drive component of drive mechanism 160. Since each of the drive connectors of surgical device 100 has a keyed and/or substantially non-rotatable interface with respective connector sleeves 218, 220 of adapter 200, when adapter 200 is coupled to surgical device 100, rotational force(s) are selectively transferred from drive mechanism 160 of surgical device 100 to adapter 200. The selective rotation of drive connector(s) of surgical device 100 allows surgical device 100 to selectively actuate different functions of loading unit 300.

Adapter 200 includes a first drive transmitting/converting assembly or first drive assembly for interconnecting a rotatable drive connector of surgical device 100 and a first axially translatable drive member 360 of loading unit 300. The first drive assembly of adapter 200 includes a first drive or clamp drive 222 and an anvil drive 250, and converts and transmits a rotation of the first rotatable drive connector of surgical device 100 to an axial translation anvil assembly 510. A second drive transmitting/converting assembly or second drive assembly of adapter 200 includes a second drive or fire and cut drive 223, a staple drive 230 and a knife drive 240, and converts and transmits a rotation of the second rotatable drive connector of surgical device 100 to an axial translation of staple pusher assembly 400 for ejecting fasteners and axial transition of a knife pusher assembly 380 for translating a knife.

More specifically, selective and independent rotation of a first drive connector of surgical device 100, and thus first connector sleeve 218 of adapter 200 corresponds to the selective and independent movement of first drive 222, which causes longitudinal movement of anvil assembly 510 relative to cartridge assembly 508. The selective and independent rotation of a second drive connector of surgical device 100, and thus second connector sleeve 220 of adapter 200 corresponds to the selective movement of second drive 223. Rotation of second drive 223 causes translation of staple drive 230 to eject fasteners from cartridge assembly 508, and also causes translation of a knife drive 240 to sever tissue. Moreover, rotation of second connector sleeve 220 in a first direction (e.g., clockwise) corresponds to rotation of second drive 223 in a second direction (e.g., counter-clockwise), which results in simultaneously longitudinally advancing staple drive 230 and longitudinally retracting knife drive 240; rotation of second connector sleeve 220 in the second, opposite direction (e.g., counter-clockwise) corresponds to rotation of second drive 223 in the first direction (e.g., clockwise), which results in simultaneously longitudinally retracting staple drive 230 and longitudinally advancing knife drive 240.

Figure 4:
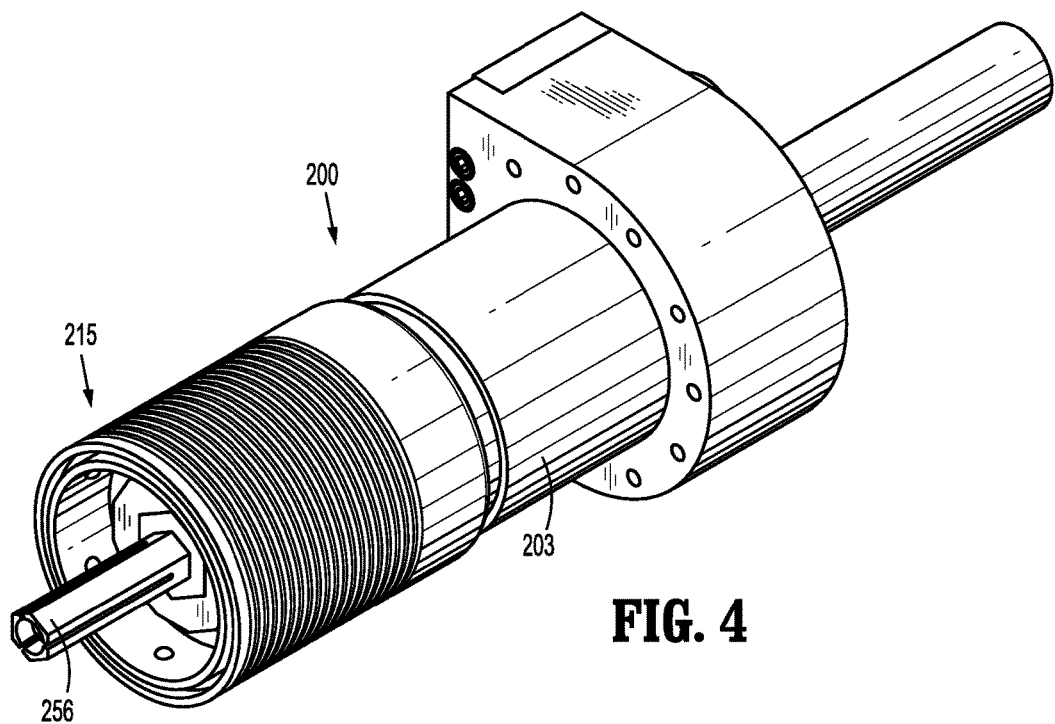

As shown in FIGS. 3 and 4, adapter 200 includes surgical device drive coupling assembly 210 (FIG. 3) at a proximal end thereof and a loading unit coupling assembly 215 (FIG. 4) at a distal end thereof. Drive coupling assembly 210 includes a drive coupling housing 210a rotatably supported, at least partially, in an adapter housing 203. In the illustrated embodiments (see FIGS. 5A, 5B and 12), drive coupling assembly 210 rotatably supports a first rotatable proximal drive shaft or element 212 and a second rotatable proximal drive shaft or element 214. First rotatable proximal drive shaft 212 mates with first connector sleeve 218, and second rotatable proximal drive shaft 214 mates with second connector sleeve 220.

Figure 5A:
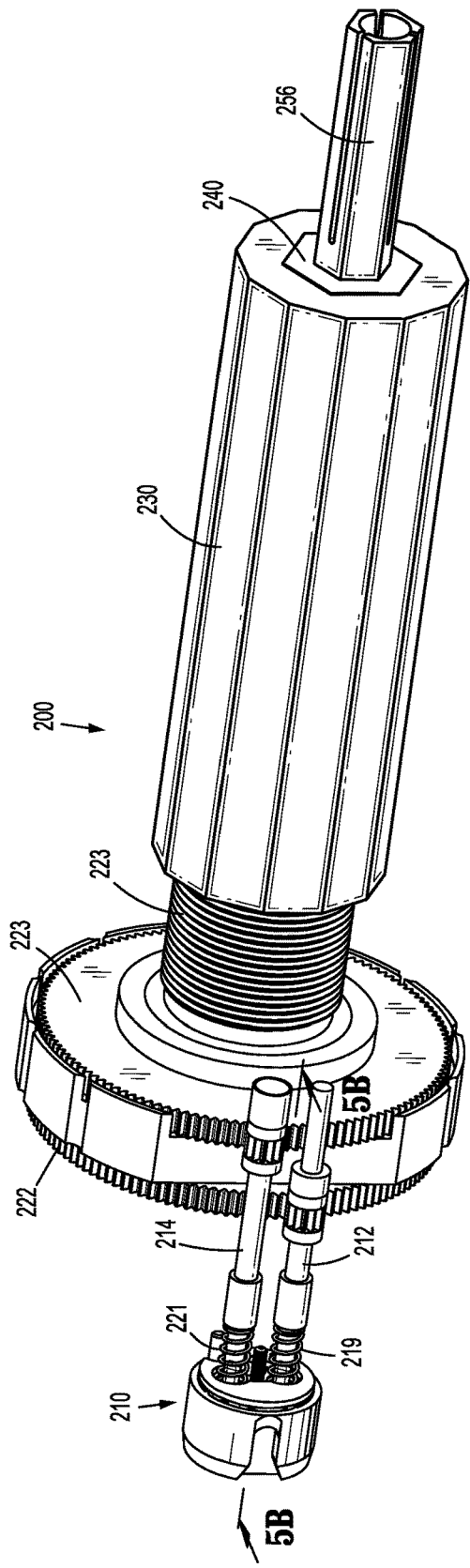
FIG. 5A is a perspective view of the surgical adapter of FIGS. 1-4 with parts removed.
Figure 5B:
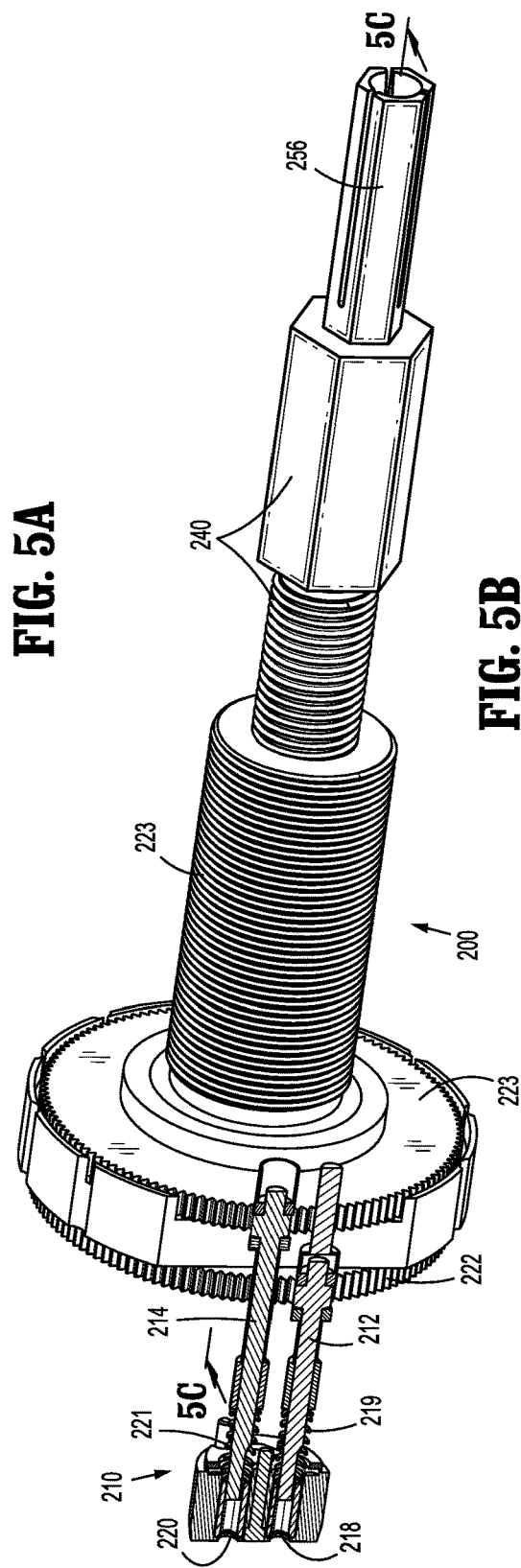
FIG. 5B is a perspective view of the surgical adapter of FIGS. 1-5A with parts removed, including a longitudinal cross-section taken along lines 5B-5B in FIG. 5A.
Figure 12:
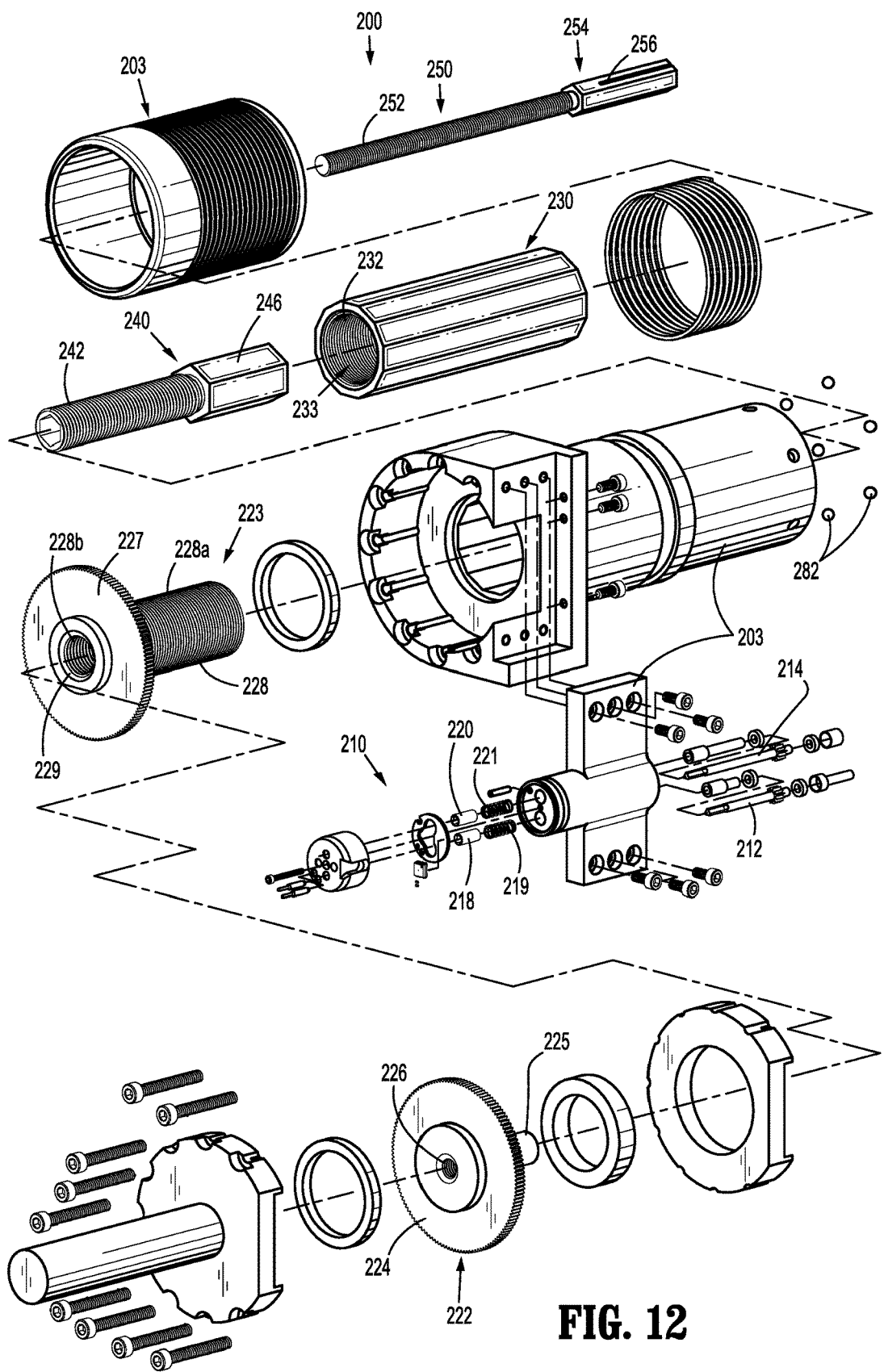
FIG. 12 is a perspective view, with parts separated, of the surgical adapter of FIGS. 1-7.

With particular reference to FIGS. 5A, 5B and 12, proximal drive coupling assembly 210 includes a first biasing member 219 and a second biasing member 221 disposed distally of respective connector sleeves 218 and 220. First biasing member 219 is disposed about first drive shaft 212, and second biasing member 221 is disposed about second drive shaft 214. Biasing members 219, 221 act on respective connector sleeves 218 and 220 to help maintain connector sleeves 218 and 220 engaged with the distal end of the respective rotatable drive connector of surgical device 100 when adapter 200 is connected to surgical device 100. In particular, biasing members 219, 221 function to bias respective connector sleeves 218, 220 in a proximal direction. In this manner, during assembly of adapter 200 to surgical device 100, if connector sleeve 218 and/or 220 is misaligned with the respective drive connector of surgical device 100, biasing members 219 and/or 221 are/is compressed. Thus, when drive mechanism 160 of surgical device 100 is engaged, the drive connectors of surgical device 100 will rotate and biasing members 219, 221 will cause connector sleeves 218, 220, respectively, to slide back proximally, effectively coupling the drive connectors of surgical device 100 to first drive shaft 212 and second drive shaft 214 of proximal drive coupling assembly 210.

Figure 8:
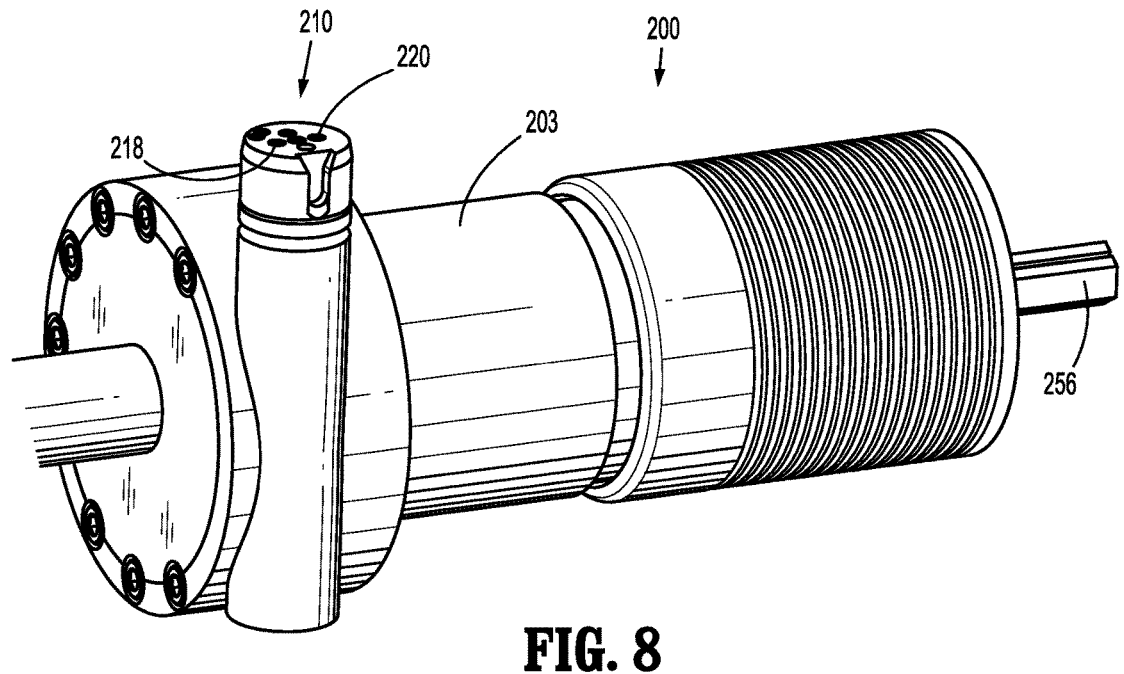
FIG. 8 is a perspective view of a second embodiment of a surgical adapter in accordance with the present disclosure.
Figure 9:
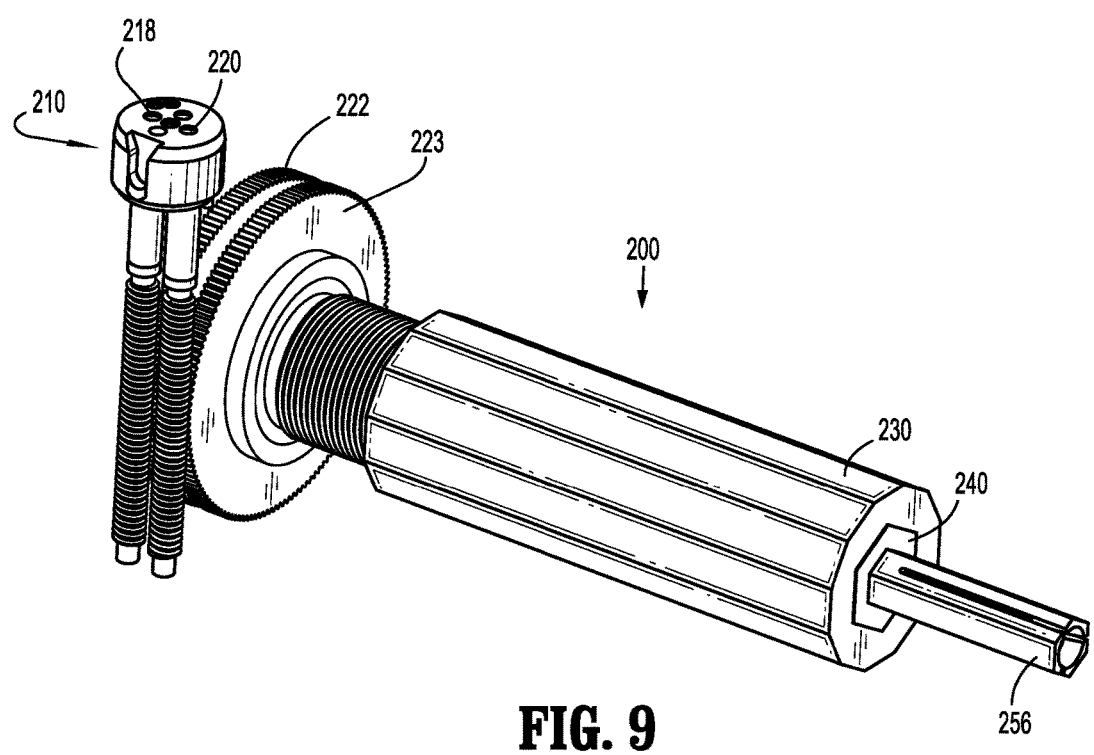
FIG. 9 is a perspective view, with parts removed, of the surgical adapter of FIG. 8.
Figure 10:
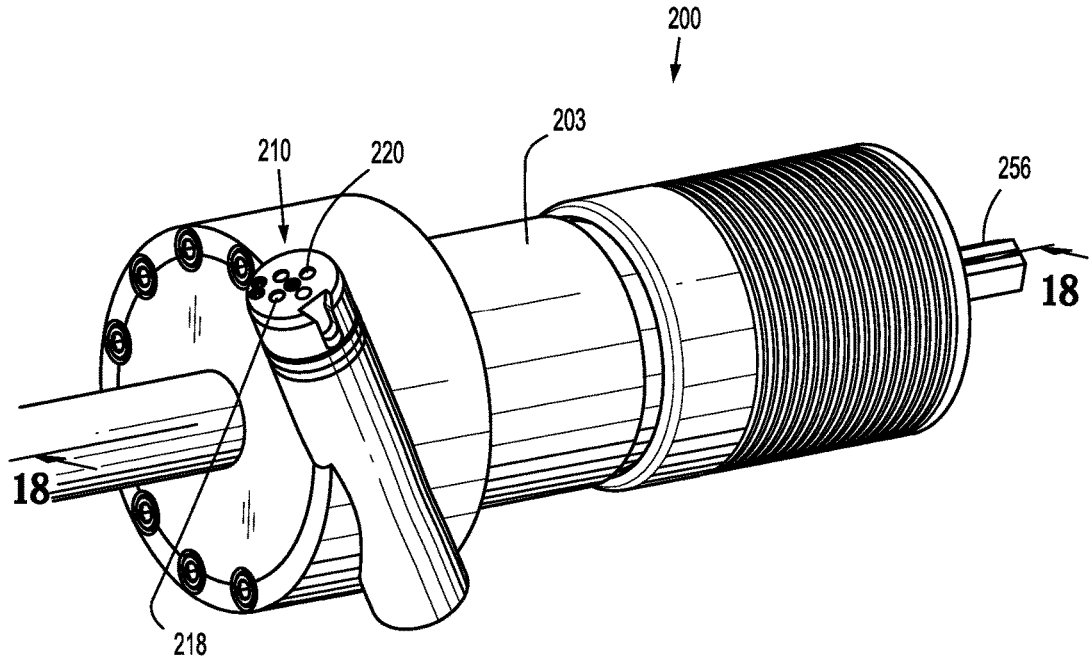
FIG. 10 is a perspective view of a third embodiment of a surgical adapter in accordance with the present disclosure.
Figure 11:
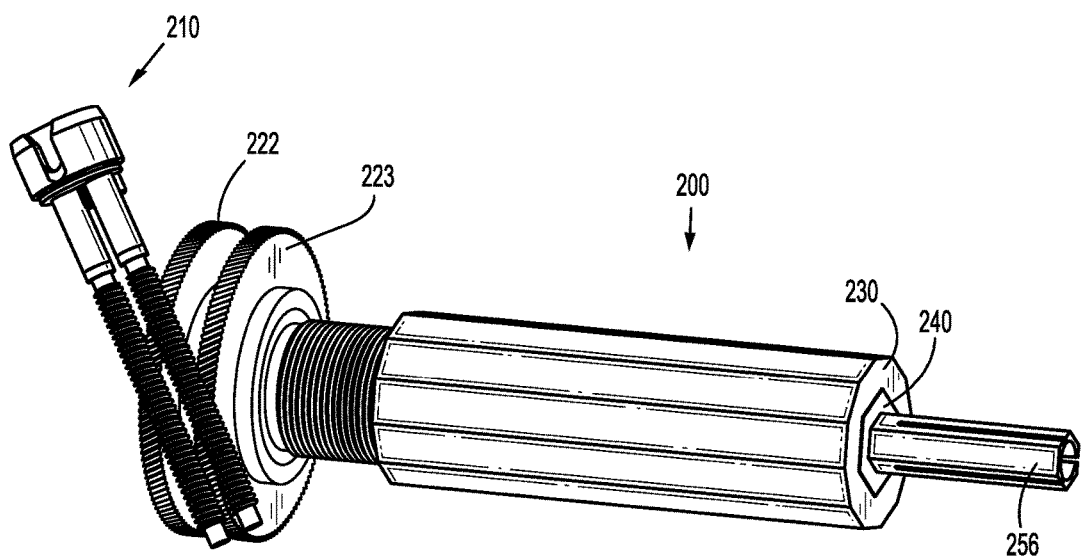
FIG. 11 is a perspective view, with parts removed, of the surgical adapter of FIG. 10.

As shown in the figures, there are several ways of orienting drive coupling assembly 210, and the components thereof, with respect to first drive 222 and second drive 223. For example, FIGS. 1-7 and 12 illustrate a liner, parallel or spur gear input, FIGS. 8-9 illustrate a 90° worm gear, and FIGS. 10-11 and 18-21 illustrate an angled input. As can be appreciated, the functions and operation of surgical device 100, adapter 200, and loading unit 300 are similar in each of these embodiments. Thus, only the details of the embodiment illustrated in FIGS. 1-7 and 12 will be discussed herein. As can be appreciated, a parallel drive can be accomplished using cylindrical gears, a drive perpendicular to the input (e.g., a 90° worm gear) can be accomplished using worm gears, and an angled input drive can be accomplished using other gear sets.

Figure 5C:
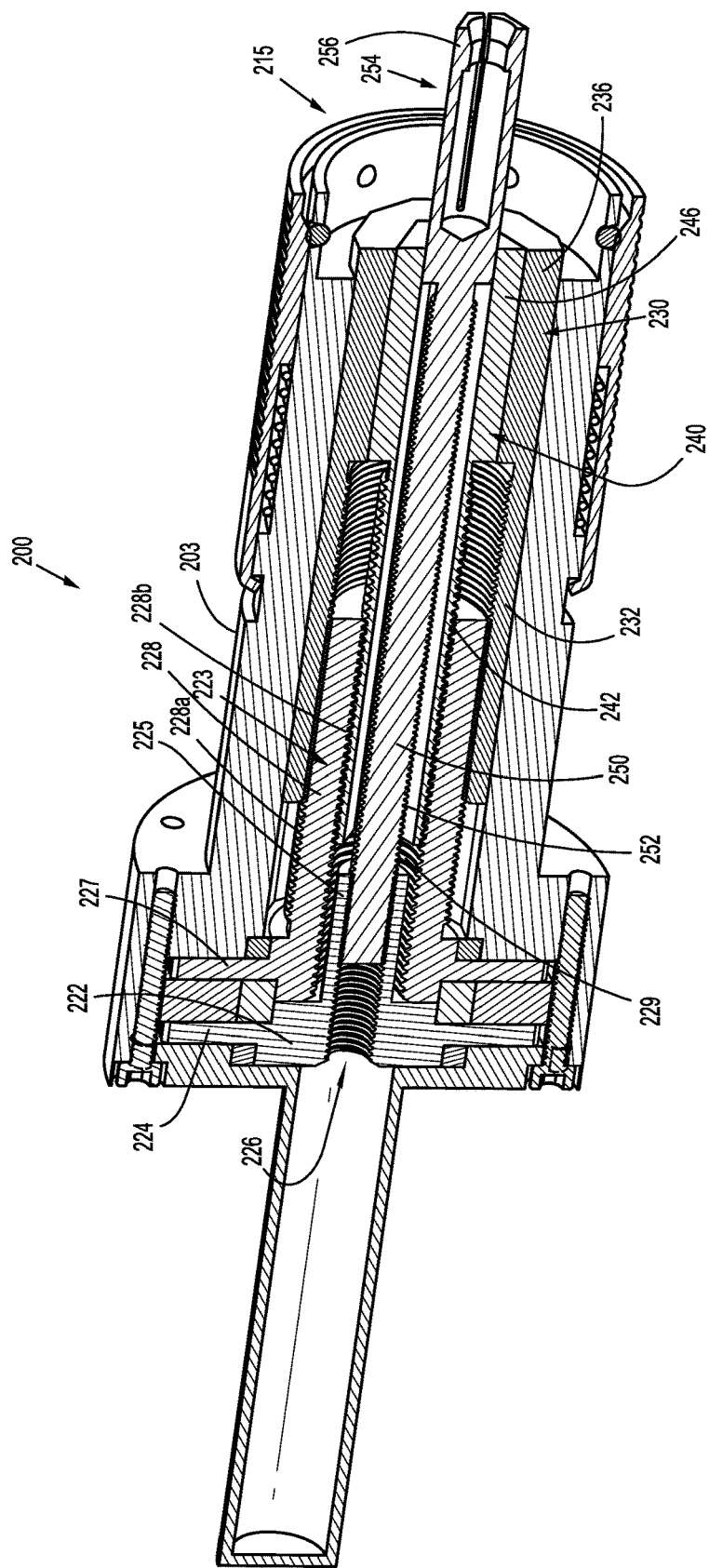
FIG. 5C is a longitudinal cross-sectional and perspective view of the surgical adapter of FIGS. 1-5B taken along lines 5C-5C in FIG. 5B.
Figure 6:
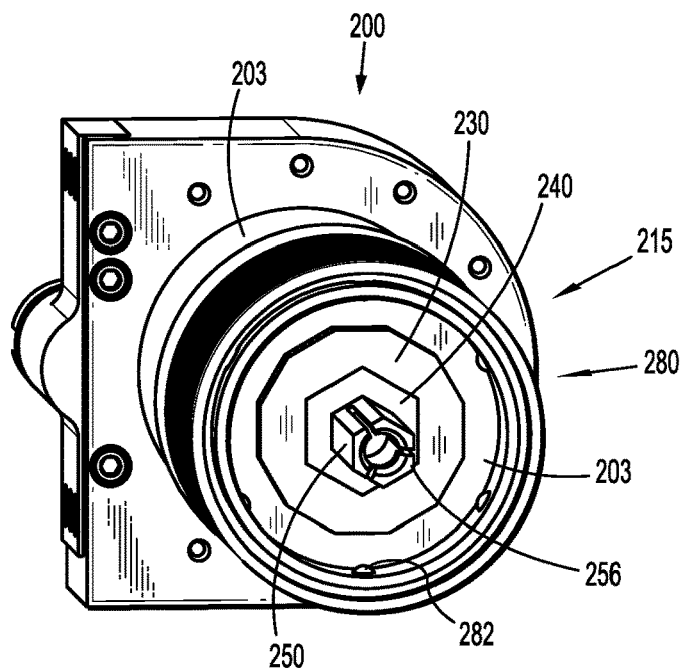
FIGS. 6 and 7 are perspective views of distal portions of the surgical adapter of FIGS. 1-5C.
Figure 7:
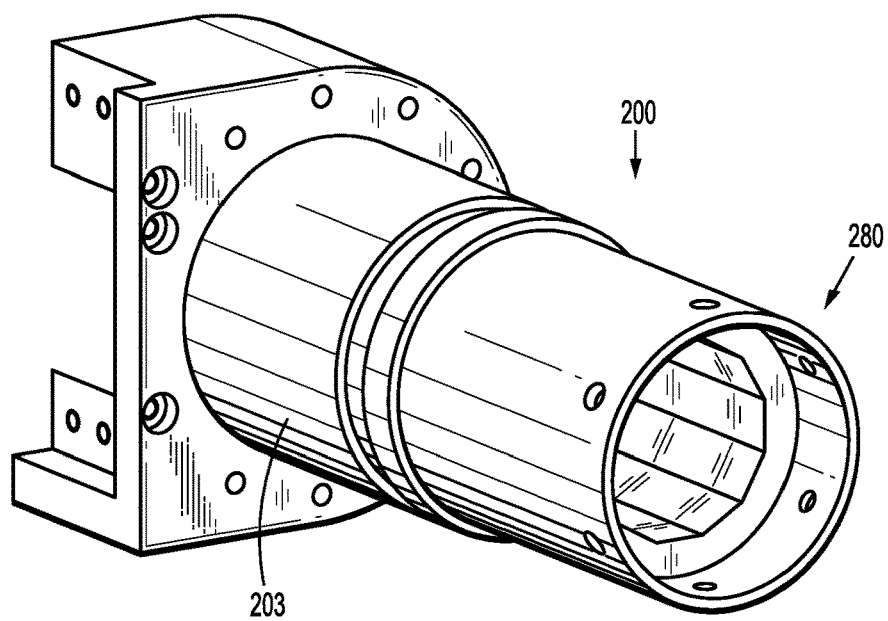

With particular reference to FIGS. 5C and 12, the first drive assembly, which is mechanically engaged with first drive shaft 212, includes clamp drive 222 and anvil drive 250. Clamp drive 222 includes a drive nut 224, a distal drive member 225 extending distally from drive nut 224, and a threaded bore 226 extending through drive nut 224 and distal drive member 225. A perimeter of drive nut 224 is threaded for engaging threads on a distal portion of first drive shaft 212. Anvil drive 250 includes a proximal, threaded portion 252, and a distal section 254 including a collet 256 for mechanically engaging a proximal portion 362 of a trocar assembly 360 of loading unit 300. At least part of threaded portion 252 of anvil drive 250 extends at least partially through threaded bore 226 of clamp drive 222. As such, rotation of first drive shaft 212, causes rotation of clamp drive 222, which causes longitudinal translation of anvil drive 250, which results in movement of anvil assembly 510 relative to cartridge assembly 508, as discussed in further detail below.

With continued reference to FIGS. 5C and 12, the second drive assembly, which is mechanically engaged with second drive shaft 214, includes second drive 223, staple drive 230 and knife drive 240. Second drive 223 includes a drive nut 227, a distal drive member 228 extending distally from drive nut 227, and an inner bore 229 extending through distal drive member 228. Distal drive member 228 includes a first set of threads 228a disposed around an outer perimeter thereof, and a second set of threads 228b disposed around an inner perimeter thereof, adjacent inner bore 229. First set of threads 228a are threaded in an opposite orientation from second set of threads 228b. For example, first set of threads 228a are right-handed threads, and second set of threads 228b are left-handed threads, or vice versa. A perimeter of drive nut 227 is threaded for engaging threads on a distal portion of second drive shaft 214.

Staple drive 230 includes a proximal, threaded portion 232, and a distal section 236. The threads of threaded portion 232 surround a bore 233 (FIG. 12), which is configured to accept at least a portion of distal drive member 228 of second drive 223 therein. Threaded portion 232 of staple drive 230 is configured to mechanically engage first set of threads 228a of second drive 223. Knife drive 240 includes a proximal, threaded portion 242, and a distal section 246. The threads of threaded portion 242 are configured to mechanically engage second set of threads 228b of second drive 223.

As such, rotation of second drive shaft 214 in a first direction (e.g., clockwise), causes rotation of second drive 223 in a second, opposite direction (e.g., counter-clockwise), which causes distal translation of staple drive 230, which results in the ejection of fasteners from cartridge assembly 508, as discussed in further detail below, and which causes proximal translation of knife drive 240. Further, rotation of second drive shaft 214 in the second direction (e.g., counter-clockwise) causes rotation of second drive 223 in the first, opposite direction (e.g., clockwise), which causes proximal translation of staple drive 230, and which causes distal translation of knife drive 240, which results in the distal advancement of a knife blade to sever tissue, as discussed in further detail below. As can be appreciated, the opposite orientation of threads of first set of threads 228a and second set of threads 228b enables the two directions of rotation of second drive 223 to cause the two different elements (i.e., staple drive 230 and knife drive 240) to move in opposite directions from each other. Additionally, it is envisioned that the threads 228a, 228b are of different pitches from each other, for example to increase longitudinal displacement and provide lower forces, and/or to decrease longitudinal displacement and increase the generated force.

Additionally, each of anvil drive 250, staple drive 230, knife drive 240 and adapter housing 203 includes anti-rotation features that are produced by a non-circular cross-sectional shape. For instance, and with particular reference to FIG. 6, a distal portion of anvil drive 250 includes an outer diameter having a hexagonal cross-section which mates with a corresponding hexagonal cross-section of in inner diameter of knife drive 240. An outer diameter of knife drive 240 includes a hexagonal cross-section which mates with a corresponding hexagonal cross-section of an inner diameter of staple drive 230. An outer diameter of staple drive 230 includes a dodecagonal (12-sided polygon) cross-section which mates with a corresponding dodecagonal cross-section of an inner diameter of adapter housing 203. Thus, all the linear drives (staple drive 230, knife drive 240 and anvil drive 250) are rotationally locked to adapter housing 203. Other non-circular shapes and features can be used to accomplish anti-rotation such as a key way, splines etc.

Referring now to FIGS. 13-23, further details of loading unit 300 are discussed herein. Loading unit 300 includes a proximal hub 310, an elongated portion 350 extending distally from proximal hub 310, and an end effector 500 disposed adjacent a distal end 302 of elongated portion 350. Proximal hub 310 is configured to mate with a distal portion 280 (FIGS. 6, 7, 20 and 21) of adapter 200. More specifically, proximal hub 310 includes a plurality of detents 312, which are configured to receive corresponding balls 282 (FIGS. 6, 12, 20 and 23) from distal portion 280 of adapter 200, which fixes rotation and axial displacement between adapter 200 and loading unit 300. Additionally, the ball 282/detent 312 interface enables loading unit 300 to be rotated and locked in a plurality of radial positions with respect to adapter 200.

Figure 16:
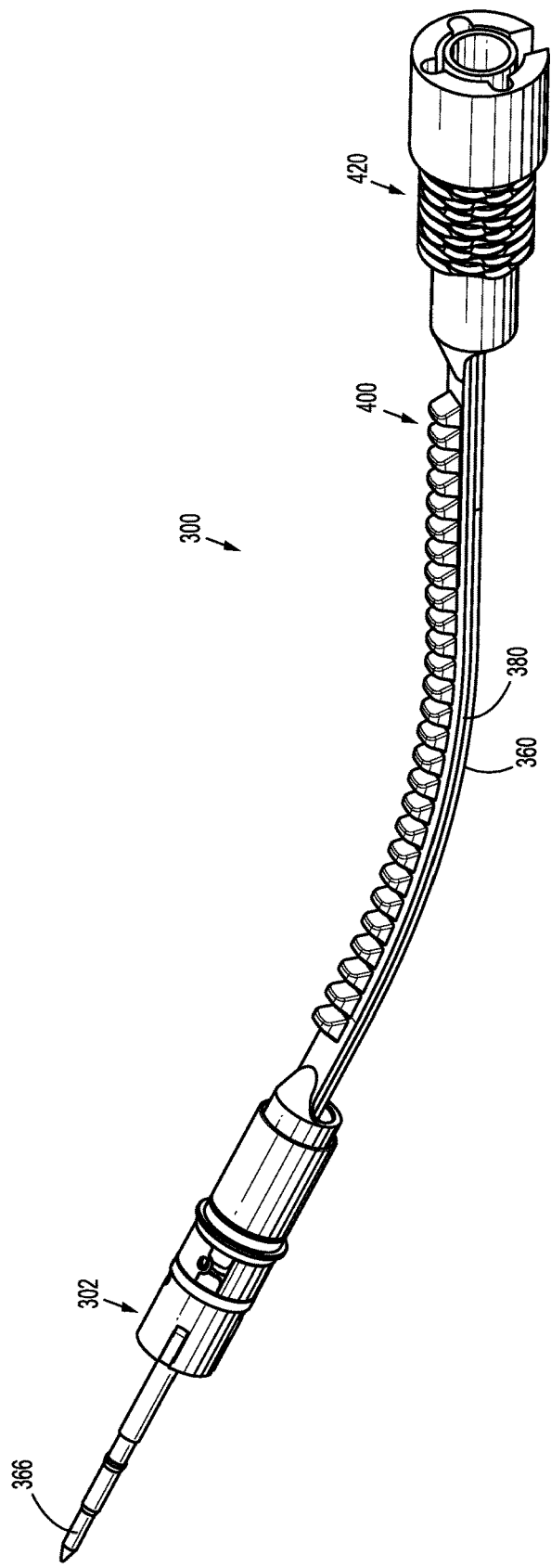
FIG. 16 is a perspective view of the tube assembly of FIGS. 13 and 14 with parts removed.
Figure 17:
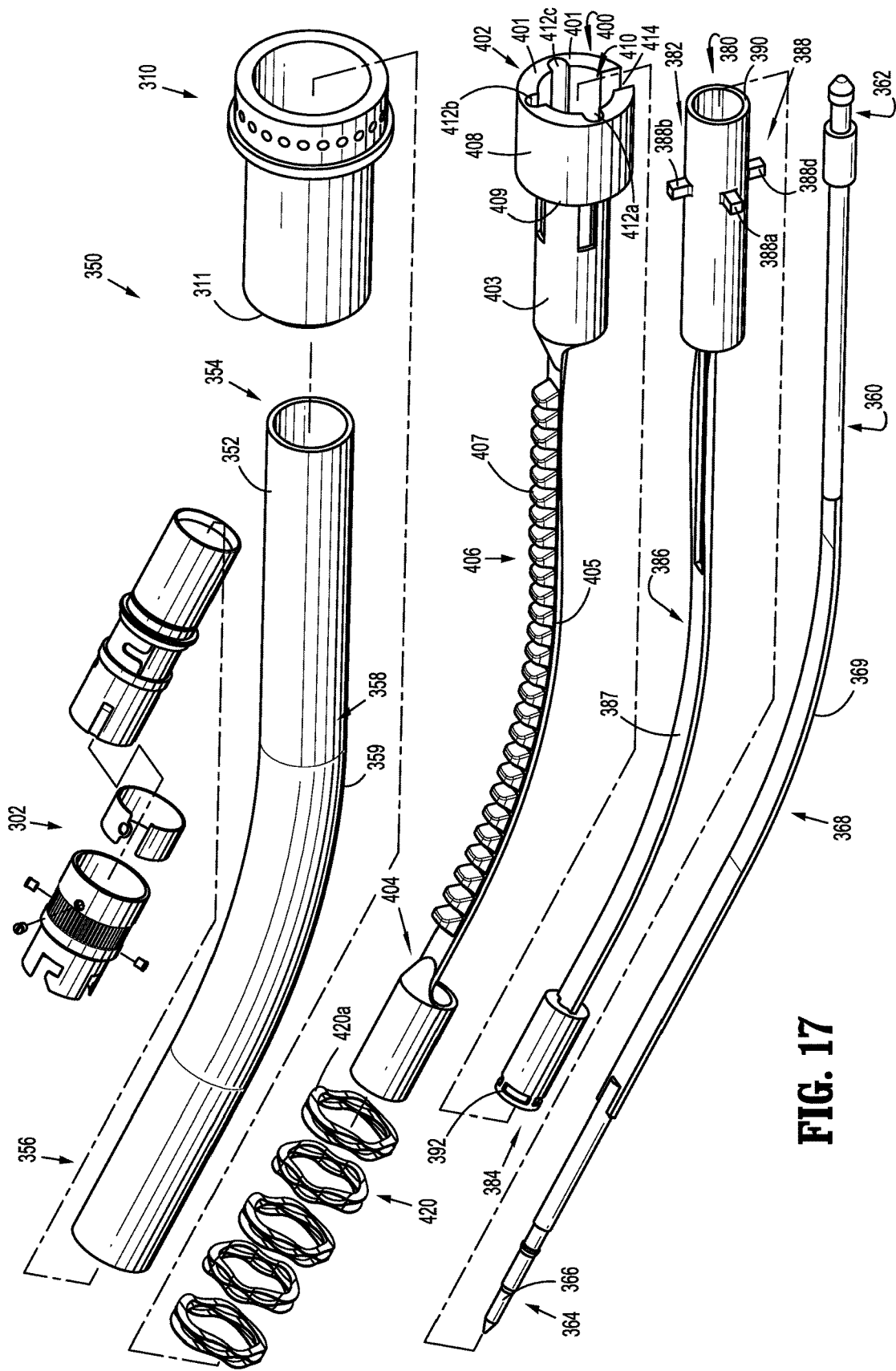
FIG. 17 is a perspective view of the tube assembly of FIGS. 13-16 with parts separated.
Figure 18:
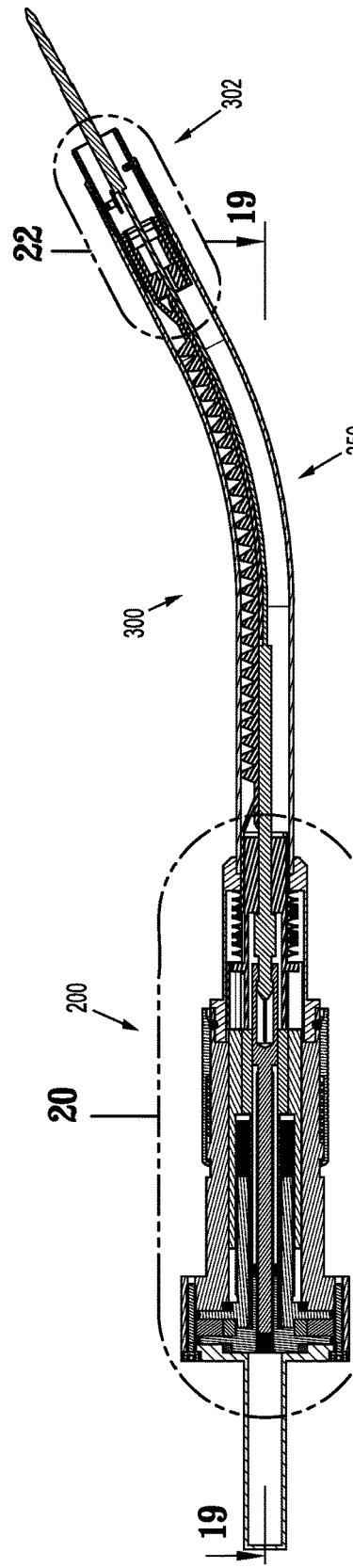
FIG. 18 is a cross-sectional view of the tube assembly of FIGS. 13-17.
Figure 19:
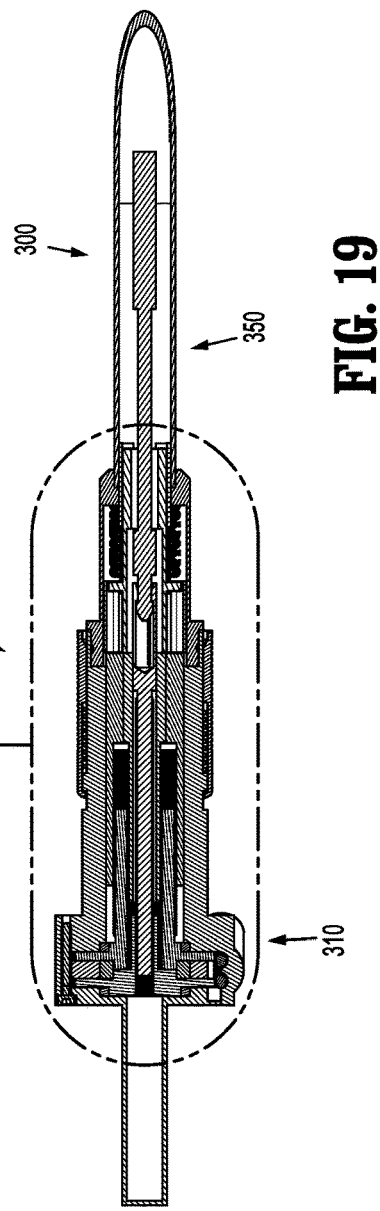
FIG. 19 is a cross-sectional view of the tube assembly taken along line 19-19 of FIG. 18.
Figure 22:
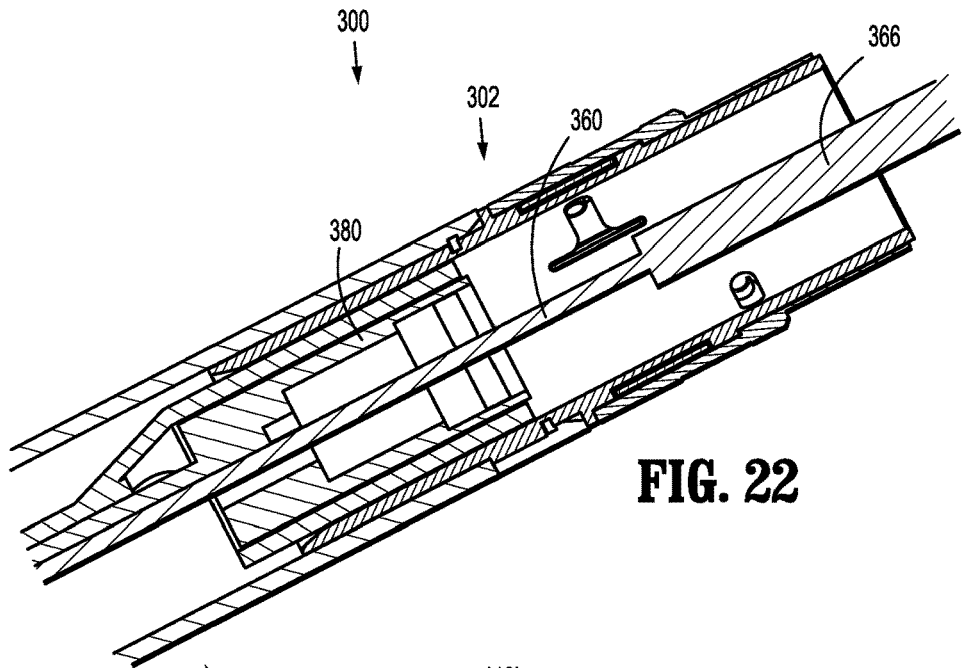
FIG. 22 is an enlarged view of the area of detail depicted in FIG. 18.
Figure 23:
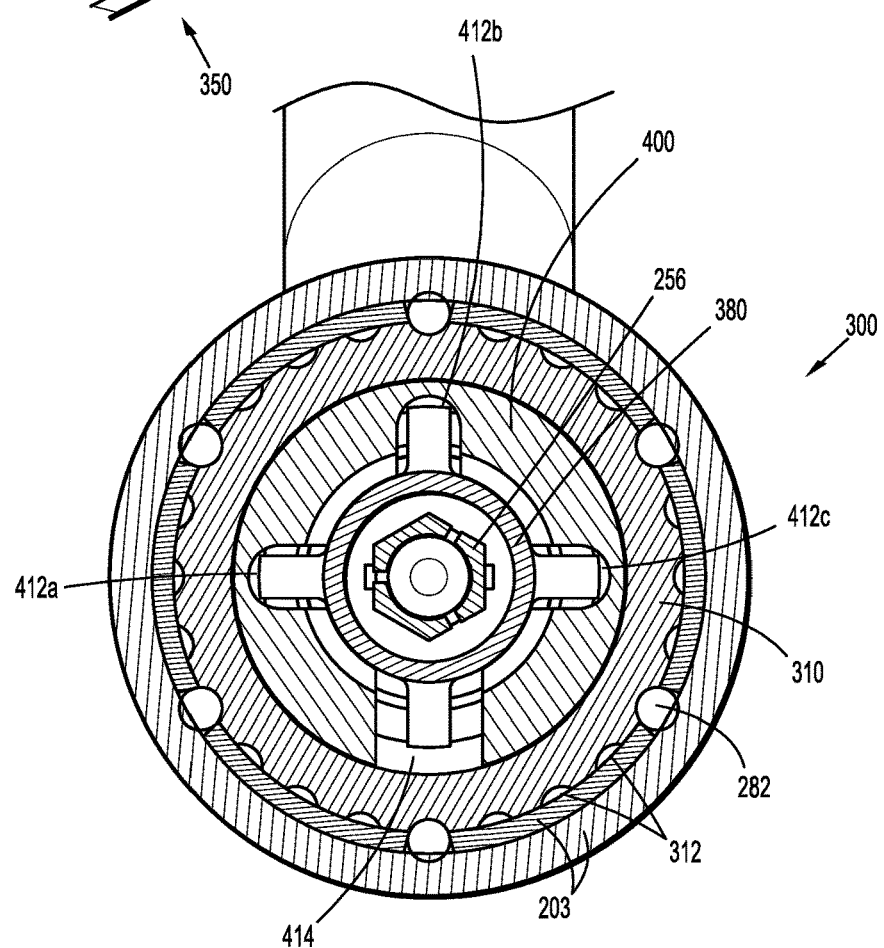
FIG. 23 is a radial cross-sectional view taken along line 23-23 in FIG. 20.

With reference to FIGS. 16 and 17, elongated portion 350 of loading unit 300 includes an outer tube 352 (FIG. 17), a trocar assembly 360, knife pusher assembly 380, staple pusher assembly 400, and a plurality of biasing elements 420. With particular reference to FIG. 16, a proximal portion 362 of trocar assembly 360 is configured for insertion at least partially into collet 256 of adapter 200 (see FIGS. 20 and 21). A distal portion 364 of trocar assembly 360 includes an end effector attachment 366, which is configured to removably attach to an anvil 510 of end effector 500 (see FIGS. 1 and 2). An intermediate portion 368 of trocar assembly 360 interconnects proximal portion 362 and distal portion 364, and, in the illustrated embodiment, includes a longitudinally curved portion 369. Intermediate portion 368 transfers longitudinal forces acting on proximal portion 362 to distal portion 364.

Knife pusher assembly 380 includes a proximal portion 382, a distal portion 384, and an intermediate portion 386 interconnecting proximal portion 382 and distal portion 384. Proximal portion 382 includes a spring interface 388, and a proximal face 390 for engaging a distal face 247 of knife drive 240 (FIGS. 20-21). As shown, spring interface 388 includes four sections 388a, 388b, 388c and 388d (see FIGS. 17, 20 and 21) evenly spaced around the perimeter of proximal portion 382 and are configured for engaging a proximal-most biasing element 420a. Other configurations of spring interface 388 are also envisioned by the present disclosure. Distal portion 384 of knife pusher assembly 380 includes a knife pusher 392, which is configured to engage a knife (e.g., be advanced into contact with a knife) of end effector 500. Intermediate portion 386, which in the illustrated embodiment includes a longitudinally curved portion 387, transfers longitudinal forces acting on proximal portion 382 to distal portion 384.

Staple pusher assembly 400 includes a proximal portion 402, a distal portion 404, and an intermediate portion 406 interconnecting proximal portion 402 and distal portion 404. Proximal portion 402 includes a hub 408 and a distal extension 403 extending distally from hub 408. Hub 408 and distal extension 403 include a bore 410 extending therethrough. Bore 410 includes three slots 412a, 412b and 412c and a slit 414, which extend through a wall of hub 408 and which extend partially through distal extension 403. Slots 412a-412c are configured and dimensioned to allow sections 388a, 388b and 388c of spring interface 388 to longitudinally slide at least partially through hub 408 and distal extension 403. Slit 414 is configured and dimensioned to allow section 388d of spring interface 388 to longitudinally slide at least partially through hub 408 and distal extension 403. In the illustrated embodiment, intermediate portion 406 includes a longitudinally curved portion and includes a plurality of ribs 407 along at least a portion of its length. It is envisioned that, when assembled, ribs 407 abut or substantially abut an inner wall of outer tube 352, such that when staple pusher assembly 400 is longitudinally advanced with respect to outer tube 352, ribs 407 ride along the inner wall of outer tube 352 to help resist the inward radial forced applied. Intermediate portion 406 of staple pusher assembly 400 interconnects proximal portion 402 and distal portion 404, and, in the illustrated embodiment, includes a longitudinally curved portion 405. Intermediate portion 406 transfers longitudinal forces acting on proximal portion 402 to distal portion 404.

Outer tube 352 includes a proximal portion 354 that mechanically engages proximal hub 310, and a distal portion 356 that mechanically engages end effector 500. An intermediate portion 358 of outer tube 352 interconnects proximal portion 354 and distal portion 356, and in the illustrated embodiment, includes a longitudinally curved portion 359.

With continued reference to FIGS. 17-23, when loading unit 300 is assembled, proximal portion 362 of trocar assembly 360 is disposed within proximal portion 382 of knife pusher assembly 380, at least part of distal portion 364 is disposed within distal portion 384 of knife pusher assembly 380, intermediate portion 368 is disposed adjacent intermediate portion 386 of knife pusher assembly 380, and end effector attachment 366 extends distally beyond distal portion 384 of knife pusher assembly 380.

Additionally, when loading unit 300 is assembled, proximal portion 382 of knife pusher assembly 380 is disposed at least partially within proximal portion 402 of staple pusher assembly 400, distal portion 384 of knife pusher assembly 380 is disposed at least partially within distal portion 404 of staple pusher assembly 400, and intermediate portion 386 of knife pusher assembly 380 is disposed adjacent intermediate portion 406 of staple pusher assembly 400. Further, sections 388a-c of spring interface 388 are positioned within respective slots 412a-412c of bore 410, and section 388d of spring interface 388 is positioned within slit 414 of hub 410.

Biasing elements 420 are positioned distally of spring interface 388 of loading unit 300, distally of a distal face 409 of hub 408 of staple pusher assembly 400, and proximally of a distal wall 311 of proximal hub 310. Biasing elements 420 bias both knife pusher assembly 380 and staple pusher assembly 400 proximally (i.e., toward their retracted positions). More particularly, when staple pusher assembly 400 is distally advanced (as discussed above), biasing elements 420 are compressed between distal face 409 of hub 408 and distal wall 311 of proximal hub 310. Additionally, when knife pusher assembly 380 is advanced (as discussed above), biasing elements are compressed between spring interface 388 of knife pusher assembly 380 and distal wall 311 of proximal hub 310. Moreover, slots 412a-412c and slit 414 of hub 408 and distal extension 403 accommodate spring interface 388 and allow spring interface 388 to longitudinally slide therethrough, which helps enable knife pusher assembly 380 to longitudinally translate with respect to staple pusher assembly 400.

Additionally, when loading unit 300 is assembled, trocar assembly 360, knife pusher assembly 380, stapler pusher assembly 400 and biasing elements 420 are all at least partially disposed within proximal hub 310 and/or outer tube 352.

In accordance with the descriptions above, the use of surgical device 100 is described herein. In particular, rotation of first drive shaft 212, causes rotation of clamp drive 222, which causes longitudinal translation of anvil drive 250, which results in a corresponding longitudinal translation of trocar assembly 360, which results in end effector attachment 366 longitudinally translating to move anvil assembly 510 relative to cartridge assembly 508 (e.g., to clamp tissue therebetween). Collectively, anvil drive 250 and trocar assembly 360 are a drive element.

Rotation of second drive shaft 214 in a first direction (e.g., clockwise), causes rotation of second drive 223 in a second, opposite direction (e.g., counter-clockwise), which causes distal translation of staple drive 230, which causes corresponding distal translation of staple pusher assembly 400 (via the engagement between distal face 231 of staple drive 230 and a proximal face 401 of staple pusher assembly 400), which results in fasteners being ejected from end effector 500 (e.g., at least partially through tissue). Additionally, rotation of second drive shaft 214 in the first direction causes proximal translation of knife drive 240. Collectively, staple drive 230 and staple pusher assembly 400 are a drive element.

Rotation of second drive shaft 214 in the second direction (e.g., counter-clockwise) causes rotation of second drive 223 in the first, opposite direction (e.g., clockwise), which causes proximal translation of staple drive 230, and which causes distal translation of knife drive 240. Distal translation of knife drive 240 causes corresponding distal translation of knife pusher assembly 380 (via the engagement between distal face 247 of knife drive 240 and proximal face 390 of knife pusher assembly 380), which results in the distal advancement of knife pusher 392 and a knife (e.g., to sever tissue). Collectively, knife drive 240 and knife pusher assembly 380 are a drive element.

While the above description discusses a powered rotation of drive shafts 212, 214 (e.g., with the power supplied by a battery), the present disclosure also includes using the disclosed drive assemblies with manually-operated handle assemblies (e.g., including a rotatable knob). In such embodiments, it is envisioned that rotating the knob is a first direction results in fasteners being ejected from the surgical instrument, and rotating the knob in a second, opposite direction results in distal advancement of a knife to sever tissue. An example of a surgical instrument including a rotatable knob is disclosed in U.S. Pat. No. 8,317,075 by Milliman ("Milliman"), the entire contents of which are hereby incorporated by reference herein. Additionally, Milliman discloses further details of end effector 500.

While the above description discusses a surgical device 100 including a particular type of end effector 500 (i.e., where anvil assembly 510 is longitudinally translatable with respect to cartridge assembly 508), other types of end effectors are also contemplated (e.g., loading units including at least one pivotable jaw member).

Additionally, the present disclosure includes method of using surgical device 100, and components thereof, as described herein.

It will be understood that various modifications may be made to the embodiments of the presently disclosed surgical device and adapter. Therefore, the above description should not be construed as limiting, but merely as exemplifications of particular embodiments. Those skilled in the art will envision other modifications within the scope and spirit of the claims appended hereto.

The invention claimed is:

1. A surgical device comprising:
an adapter including:
a first shaft configured to receive first rotational input from an actuation mechanism;
a first drive rotatably coupled with the first shaft;
a first axial member operatively coupled with the first drive such that rotation of the first drive causes axial displacement of the first axial member;
a second shaft configured to receive second rotational input from the actuation mechanism; a second drive rotatably coupled with the second shaft; and
second and third axial members operatively coupled with the second drive such that rotation of the second drive in a first direction causes axial displacement of the second axial member in a third direction and rotation of the second drive in a second direction opposite of the first direction causes axial displacement of the third axial member in the third direction; and
an end effector including first, second, and third axial drives configured for axial displacement to effect first, second, and third functions of the end effector, the first, second, and third axial drives operatively coupled to the respective first, second, and third axial members of the adapter.

2. The surgical device according to claim 1, wherein the first shaft defines an acute angle with the first drive.

3. The surgical device according to claim 2, wherein the first shaft includes a worm gear.

4. The surgical device according to claim 1, wherein the first shaft includes a spur gear.

5. The surgical device according to claim 1, wherein the second and third axial members are coaxially arranged.

6. The surgical device according to claim 1, wherein the end effector includes a plurality of fasteners therein, distal translation of the second axial member causing the plurality of fasteners to be ejected from the end effector.

7. The surgical device according to claim 1, wherein the end effector includes a knife therein, axial displacement of the third axial member causing translation of the knife.

8. The surgical device according to claim 1, wherein the end effector includes an anvil movable between open and approximated positions, axial displacement of the first axial member transitioning the anvil between the open and approximated positions.

9. The surgical device according to claim 1, wherein the second drive includes first and second portions configured to engage the second and third axial members, respectively.

10. The surgical device according to claim 9, wherein the first and second portions of the second drive are formed as a single construct.

11. The surgical device according to claim 9, wherein the first and second portions of the second drive include a set of right-handed threads and a set of left-handed threads, respectively.

12. The surgical device according to claim 11, wherein the right-handed threads are disposed on an outer surface of the second drive and the left-handed threads are disposed on an inner surface of the second drive.

13. The surgical device according to claim 1, wherein at least one of the first or second shafts is proximally biased.

14. An adapter for mechanically engaging a powered surgical instrument, comprising:
 a first shaft configured to receive first rotational input from an actuation mechanism;
 a first drive rotatably coupled with the first shaft;
 a first axial member operatively coupled with the first drive such that rotation of the first drive causes axial displacement of the first axial member;
 a second shaft configured to receive second rotational input from the actuation mechanism;
 a second drive rotatably coupled with the second shaft; and
 second and third axial members operatively coupled with the second drive such that rotation of the second drive in a first direction causes axial displacement of the second axial member in a third direction and rotation of the second drive in a second direction opposite of the first direction causes axial displacement of the third axial member in the third direction, wherein the first, second, and third axial members are configured to be operatively coupled with an end effector of the powered surgical instrument such that axial displacement of the first, second, and third axial members effects first, second, and third functions of the end effector, respectively.

15. The adapter according to claim 14, wherein the first shaft defines an acute angle with the first drive.

16. The adapter according to claim 15, wherein the first shaft includes a worm gear.

17. The adapter according to claim 14, wherein the first shaft includes a spur gear.

18. The adapter according to claim 14, wherein the second drive includes first and second portions configured to engage the second and third axial members, respectively.

19. The adapter according to claim 18, wherein the first and second portions of the second drive are formed as a single construct.

* * * * *